US012797640B2

(12) United States Patent
Suhonen et al.

(10) Patent No.: US 12,797,640 B2
(45) Date of Patent: Nov. 17, 2026

(54) SYSTEMS AND METHODS FOR GENERATING PLAN QUALITY SCORES TO OPTIMIZE RADIOTHERAPY TREATMENT PLANNING

(71) Applicant: Siemens Healthineers International AG, Steinhausen (CH)

(72) Inventors: Pauli Mikael Suhonen, Helsinki (FI); Jarkko Peltola, Tuusula (FI)

(73) Assignee: Siemens Healthineers International AG, Steinhausen (CH)

(*) Notice: Subject to any disclaimer, the term of this patent is extended or adjusted under 35 U.S.C. 154(b) by 895 days.

(21) Appl. No.: 18/086,354

(22) Filed: Dec. 21, 2022

(65) Prior Publication Data

US 2024/0207643 A1 Jun. 27, 2024

(51) Int. Cl.
*A61N 5/10* (2006.01)
*G16H 20/40* (2018.01)

(52) U.S. Cl.
CPC ........... *A61N 5/1031* (2013.01); *G16H 20/40* (2018.01)

(58) Field of Classification Search
CPC ....... A61N 5/1031; A61N 5/103; G16H 20/40
USPC .............................................................. 600/1
See application file for complete search history.

(56) References Cited

U.S. PATENT DOCUMENTS

2012/0310615 A1* 12/2012 Moore ..................... G06N 5/04 703/11
2015/0095044 A1* 4/2015 Hartman ................ A61N 5/103 705/2
2018/0185669 A1 7/2018 Kuusela et al.
2020/0206532 A1* 7/2020 Kuusela ................. A61N 5/103
2020/0289847 A1* 9/2020 Sjölund ................ G06N 3/0464
2021/0069527 A1 3/2021 Peltola et al.
(Continued)

FOREIGN PATENT DOCUMENTS

CN 105765586 A * 7/2016 ............. G16H 50/20
CN 107708808 B * 10/2020 ............. G16H 20/40
(Continued)

OTHER PUBLICATIONS

L Xing, J G Li, S Donaldson, Q T Le and A L Boyer, Optimization of importance factors in inverse planning Phys. Med. Biol. 44 (1999) 2525-2536.*
(Continued)

*Primary Examiner* — Brian L Casler
(74) *Attorney, Agent, or Firm* — Foley & Lardner LLP

(57) ABSTRACT

Systems and methods for radiation treatment planning can include a computing system receiving one or more indications of one or more clinical objectives for a radiotherapy treatment plan, and determining, for each clinical objective, a corresponding quality metric interval. The computing system can determine within each quality metric interval, a corresponding sub-score function having a derivative determined based on one or more priorities of the one or more clinical objectives, and determine a quality score function for the radiotherapy treatment plan by aggregating sub-score functions within quality metric intervals corresponding to the one or more clinical objectives. The computing system can use the quality score function to adjust one or more parameters of an objective function for optimizing the radiotherapy plan.

20 Claims, 7 Drawing Sheets

(56) References Cited

U.S. PATENT DOCUMENTS

| | | | |
|---|---|---|---|
| 2022/0241611 | A1 | 8/2022 | Bokrantz et al. |
| 2024/0212822 | A1 | 6/2024 | Peltola et al. |

FOREIGN PATENT DOCUMENTS

| | | | | |
|---|---|---|---|---|
| EP | 3 418 926 | A1 | 12/2018 | |
| EP | 3 673 956 | A1 | 7/2020 | |
| WO | WO-2005021085 | A2 * | 3/2005 | ........... A61N 5/1031 |
| WO | WO-2012024448 | A2 * | 2/2012 | ............. A61N 5/103 |

OTHER PUBLICATIONS

Jacobian, Chain rule and backpropagation Apr. 4, 2018.*
European Search Report on EPO App. EP 23217924 dated Apr. 11, 2024 (2 pages).

* cited by examiner

SYSTEMS AND METHODS FOR GENERATING PLAN QUALITY SCORES TO OPTIMIZE RADIOTHERAPY TREATMENT PLANNING

FIELD OF THE DISCLOSURE

The present application relates generally to systems and methods for optimizing radiation treatment planning using plan quality scores. Specifically, the present application relates to automatically generating plan quality score function for use to optimize radiation treatment planning.

BACKGROUND

Radiotherapy is a radiation-based therapy that is used as a cancer treatment. Specifically, high doses of radiation are used to kill or shrink a tumor. The target region of a patient's body that is intended to receive radiation (e.g., tumor) is referred to as the planning target volume (PTV). The goal is to deliver enough radiation to the PTV to kill the cancerous cells. However, other organs or anatomical regions that are adjacent to, or surrounding, the PTV can be in the way of radiation beams and can receive enough radiation to damage or harm such organs or anatomical regions. These organs or anatomical regions are referred to as organs at risk (OARs). Usually a physician, a radiologist or an oncologist identifies both the PTV and the OARs prior to radiotherapy using, for example, computed tomography (CT) images, magnetic resonance imaging (MRI) images, positron emission tomography (PET) images, images obtained via some other imaging modality, or a combination thereof. For instance, the physician or the radiologist may manually mark the PTV and/or the OARs on the medical images of the patient.

Using the medical images of the patient as well as the identified PTV and the OARs, a treatment planner determines the radiation parameters to be used during the radiotherapy treatment. These radiation parameters include, for example, the type, the angle, the radiation intensity and/or the shape of each radiation beam. In determining these parameters, the treatment planner attempts to achieve a radiation dose distribution to be delivered to the patient that meets predefined criteria, e.g., set by the oncologist or the radiologist. Such criteria usually include predefined radiation dose thresholds or ranges for the PTV and the OARs to be met.

To optimize the radiation parameters in a way to meet the predefined criteria, the treatment planner usually runs a plurality of simulations with various radiation parameters, and selects a final set of radiation parameters to be used based on the simulation results. This process usually involves tweaking the radiation parameters after each simulation. Such approach is time consuming, tedious and may not provide optimal results. For instance, a patient can wait for days or weeks before a radiation therapy plan specific to the patient is ready.

SUMMARY

Embodiments described herein relate to improving radiotherapy treatment planning based on a quality score function. Radiotherapy treatment planning is usually achieved by optimizing an objective function. The objective function can represent, or can be formulated as, in terms of a set of optimization objectives that are related to, but not the same as, clinical objectives set by physicians. The clinical objectives may not be mathematically integrated into the objective function, and the radiotherapy treatment plan generated by the optimization of the objective function may not necessarily satisfy or meet the clinical objectives. Embodiments described herein can employ a quality score function representing, or formulated in terms of, the clinical objectives. A radiotherapy treatment planning system can determine a radiotherapy treatment plan by optimizing an objective function. Using the parameters of the radiotherapy treatment plan, the radiotherapy treatment planning system can evaluate the quality score function to determine a quality score of the radiotherapy treatment plan. If the quality score does not indicate a good quality plan, the radiotherapy treatment planning system can adjust or modify parameters of the objective function and run the optimization of the objective function to determine a new radiotherapy treatment plan. The radiotherapy treatment planning system can repeat adjusting the parameters of the objective function, performing the optimization of the objective function and evaluating the quality score for the determined radiotherapy treatment plan until a treatment plan with acceptable or good quality is achieved. Since the quality score function is formulated in terms of the clinical objectives, the radiotherapy treatment plan with the acceptable or good quality is expected to meet or satisfy the clinical objectives, at least to some desired extent.

According to one aspect, a method of radiation treatment planning can include one or more processors optimizing an objective function to determine a radiotherapy plan. The objective function can be defined in terms of one or more optimization objectives related to parameters of the radiotherapy plan. The method can include the one or more processors computing a quality score of the radiotherapy plan based on the parameters of the radiotherapy plan. The quality score can be defined in terms of one or more quality metrics. The method can include the one or more processors determining whether the quality score satisfies one or more criteria, and adjusting one or more parameters of the objective function upon determining that the quality score does not satisfy the one or more criteria.

In some implementations, the method can further include the one or more processors optimizing the objective function with the adjusted one or more parameters to determine a second radiotherapy plan, and computing a second quality score of the second radiotherapy plan based on second parameters of the second radiotherapy plan, determining whether the second quality score satisfies the one or more criteria, and adjusting the one or more parameters of the objective function upon determining that the second quality score does not satisfy the one or more criteria. The method can further include the one or more processors providing the second parameters of the second radiotherapy plan as output, upon determining that the second quality score satisfies the one or more criteria.

In some implementations, adjusting the one or more parameters of the objective function can include adjusting one or more weights of the one or more optimization objectives. In some implementations, the one or more quality metrics can represent one or more clinical objectives that are different from the one or more optimization objectives.

In some implementations, the method can include the one or more processors estimating an approximation of a Jacobian of the one or more quality metrics with respect to the one or more parameters of the objective function, and adjusting the one or more parameters of the objective function based on the approximation of the Jacobian. Estimating the approximation of the Jacobian of the one or more quality metrics with respect to the one or more parameters of the objective function can include at least one of (i) estimating a first approximation of the Jacobian based on intuitive relations between the one or more parameters of the objective function and the one or more quality metrics, or (ii) estimating a second approximation of the Jacobian based on one or more variations of the one or more quality metrics as the one or more parameters of the objective function are adjusted. Estimating the second approximation of the Jacobian can include modeling at least one quality metric of the one or more quality metrics as a regression model.

In some implementations, the method can include the one or more processors determining a third approximation of the Jacobian as a weighted sum of the first approximation and the second approximation, and adjusting the one or more parameters of the objective function based on the third approximation of the Jacobian. In some implementations, the method can include the one or more processors predicting a change to a quality metric of the one or more quality metrics, and adjusting a parameter of the one or more parameters of the objective function based on the predicted change to the quality metric.

According to another aspect, a radiation treatment planning system can include one or more processors and a memory to store computer code instructions. The computer code instructions, when executed, can cause the one or more processors to optimize an objective function to determine a radiotherapy plan. The objective function can be defined in terms of one or more optimization objectives related to parameters of the radiotherapy plan. The one or more processors can compute a quality score of the radiotherapy plan based on the parameters of the radiotherapy plan. The quality score can be defined in terms of one or more quality metrics. The one or more processors can determine whether the quality score satisfies one or more criteria, and adjust one or more parameters of the objective function upon determining that the quality score does not satisfy the one or more criteria.

In some implementations, the one or more processors can optimize the objective function with the adjusted one or more parameters to determine a second radiotherapy plan, compute a second quality score of the second radiotherapy plan based on second parameters of the second radiotherapy plan, determine whether the second quality score satisfies the one or more criteria, and adjust the one or more parameters of the objective function upon determining that the second quality score does not satisfy the one or more criteria. The one or more processors can provide the second parameters of the second radiotherapy plan as output, upon determining that the second quality score satisfies the one or more criteria.

In some implementations, the one or more quality metrics represent one or more clinical objectives that are different from the one or more optimization objectives. In some implementations, the one or more quality metrics can represent one or more clinical objectives that are different from the one or more optimization objectives.

In some implementations, the one or more processors can further estimate an approximation of a Jacobian of the one or more quality metrics with respect to the one or more parameters of the objective function, and adjust the one or more parameters of the objective function based on the approximation of the Jacobian. In estimating the approximation of a Jacobian of the one or more quality metrics with respect to the one or more parameters of the objective function, the one or more processors can perform at least one of (i) estimate a first approximation of the Jacobian based on intuitive relations between the one or more parameters of the objective function and the one or more quality metrics, or (ii) estimate a second approximation of the Jacobian based on one or more variations of the one or more quality metrics as the one or more parameters of the objective function are adjusted. In estimating the second approximation of the Jacobian, the one or more processors can model at least one quality metric of the one or more quality metrics as a regression model.

In some implementations, the one or more processors can determine a third approximation of the Jacobian as a weighted sum of the first approximation and the second approximation, and adjust the one or more parameters of the objective function based on the third approximation of the Jacobian. In some implementations, the one or more processors can predict a change to a quality metric of the one or more quality metrics, and adjust a parameter of the one or more parameters of the objective function based on the predicted change to the quality metric.

According to yet another aspect, a non-transitory computer-readable medium can include computer code instructions stored thereon. The computer code instructions, when executed, can cause one or more processors to optimize an objective function to determine a radiotherapy plan. The objective function can be defined in terms of one or more optimization objectives related to parameters of the radiotherapy plan. The one or more processors can compute a quality score of the radiotherapy plan based on the parameters of the radiotherapy plan. The quality score can be defined in terms of one or more quality metrics. The one or more processors can determine whether the quality score satisfies one or more criteria, and adjust one or more parameters of the objective function upon determining that the quality score does not satisfy the one or more criteria.

According to one aspect, a method of radiation treatment planning can include one or more processors receiving one or more indications of one or more clinical objectives for a radiotherapy treatment plan, and determining, for each clinical objective, a corresponding quality metric interval. The method can include the one or more processors determining, within each quality metric interval, a corresponding sub-score function having a derivative determined based on one or more priorities of the one or more clinical objectives. The method can include the one or more processors determining a quality score function for the radiotherapy treatment plan by aggregating sub-score functions within quality metric intervals corresponding to the one or more clinical objectives, and using the quality score function to adjust one or more parameters of an objective function for optimizing the radiotherapy plan.

In some implementations, using the quality score function to adjust the one or more parameters of the objective function can include assessing a first quality of a first radiotherapy plan produced by optimizing the objective function by computing a value of the quality score function based on one or more parameters of the first radiotherapy treatment plan, and adjusting the one or more parameters of the objective function in a way to increase a second quality score of a second radiotherapy treatment plan produced by optimizing the objective function with the adjusted one or more parameters.

In some implementations, each clinical objective of the one or more clinical objectives can include a constraint on a radiation dose distribution within a corresponding anatomical structure. In some implementations, the one or more indications of the one or more clinical objectives include, for each clinical objective, an indication of a priority of the clinical objective. The method can further include the one or more processors determining, for each clinical objective, a derivative of the sub-score function within the quality metric interval corresponding to the clinical objective based on the indication of the priority of the clinical objective. The higher is the priority of the clinical objective the higher is a magnitude of the derivative of the sub-score function within the quality metric interval corresponding to the clinical objective.

In some implementations, for each clinical objective of the one or more clinical objectives, the indication of the clinical objective can include an inequality related to a radiation dose distribution within a corresponding anatomical structure. The inequality can be defined in terms of a desired radiation dose value. The method can include the one or more processors determining, for each clinical objective, the corresponding quality metric interval using the desired radiation dose value. The method can include the one or more processors determining, for each clinical objective, a derivative of the sub-score function within the quality metric interval corresponding to the clinical objective based on a type of the inequality.

In some implementations, the method can include the one or more processors determining, within each quality metric interval, a corresponding score density function, and determining the sub-score function within each quality metric interval by integrating the corresponding score density function within the quality metric interval. In some implementations, the method can include the one or more processors determining, within each quality metric interval, the corresponding sub-score function as a linear function having a slope determined based the on one or more priorities of the one or more clinical objectives.

According to another aspect, a radiation treatment planning system can include one or more processors and a memory to store computer code instructions. The computer code instructions, when executed, can cause the one or more processors to receive one or more indications of one or more clinical objectives for a radiotherapy treatment plan, and determine, for each clinical objective, a corresponding quality metric interval. The one or more processors can determine within each quality metric interval, a corresponding sub-score function having a derivative determined based on one or more priorities of the one or more clinical objectives, and determine a quality score function for the radiotherapy treatment plan by aggregating sub-score functions within quality metric intervals corresponding to the one or more clinical objectives. The one or more processors can use the quality score function to adjust one or more parameters of an objective function for optimizing the radiotherapy plan.

In some implementations, in using the quality score function to adjust the one or more parameters of the objective function the one or more processors can assess a first quality of a first radiotherapy plan produced by optimizing the objective function by computing a value of the quality score function based on one or more parameters of the first radiotherapy treatment plan, and adjust the one or more parameters of the objective function in a way to increase a second quality score of a second radiotherapy treatment plan produced by optimizing the objective function with the adjusted one or more parameters.

In some implementations, each clinical objective of the one or more clinical objectives can include a constraint on a radiation dose distribution within a corresponding anatomical structure. In some implementations, the one or more indications of the one or more clinical objectives include, for each clinical objective, an indication of a priority of the clinical objective. The one or more processors can further determine, for each clinical objective, a derivative of the sub-score function within the quality metric interval corresponding to the clinical objective based on the indication of the priority of the clinical objective. The higher is the priority of the clinical objective the higher is a magnitude of the derivative of the sub-score function within the quality metric interval corresponding to the clinical objective.

In some implementations, for each clinical objective of the one or more clinical objectives, the indication of the clinical objective can include an inequality related to a radiation dose distribution within a corresponding anatomical structure. The inequality can be defined in terms of a desired radiation dose value. The one or more processors can determine, for each clinical objective, the corresponding quality metric interval using the desired radiation dose value. The one or more processors can determine, for each clinical objective, a derivative of the sub-score function within the quality metric interval corresponding to the clinical objective based on a type of the inequality.

In some implementations, the one or more processors can determine, within each quality metric interval, a corresponding score density function, and determining the sub-score function within each quality metric interval by integrating the corresponding score density function within the quality metric interval. In some implementations, the one or more processors can determine, within each quality metric interval, the corresponding sub-score function as a linear function having a slope determined based the on one or more priorities of the one or more clinical objectives.

According to yet another aspect, a non-transitory computer-readable medium can include computer code instructions stored thereon. The computer code instructions, when executed, can cause one or more processors to receive one or more indications of one or more clinical objectives for a radiotherapy treatment plan, and determine, for each clinical objective, a corresponding quality metric interval. The one or more processors can determine within each quality metric interval, a corresponding sub-score function having a derivative determined based on one or more priorities of the one or more clinical objectives, and determine a quality score function for the radiotherapy treatment plan by aggregating sub-score functions within quality metric intervals corresponding to the one or more clinical objectives. The one or more processors can use the quality score function to adjust one or more parameters of an objective function for optimizing the radiotherapy plan.

Figure 1A:
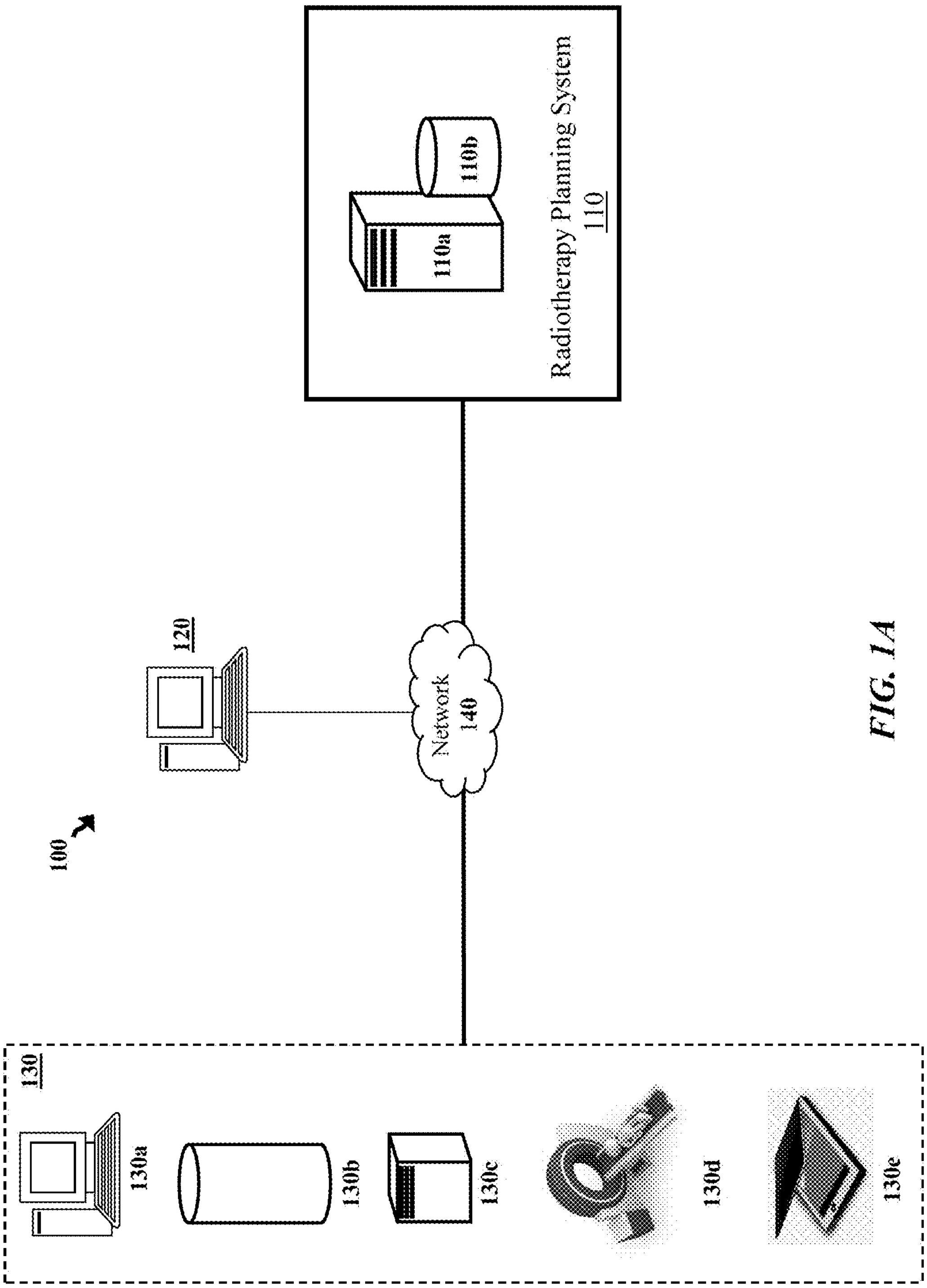
FIG. 1A shows a block diagram illustrating an example computer environment for implementing methods and processes described herein, according to an embodiment.

Some or all of the figures are schematic representations for purposes of illustration. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

DETAILED DESCRIPTION

Following below are more detailed descriptions of various concepts related to, and implementations of, methods, apparatuses, and systems for radiation treatment planning. The various concepts introduced above and discussed in greater detail below may be implemented in any of numerous ways as the described concepts are not limited to any particular manner of implementation. Examples of specific implementations and applications are provided primarily for illustrative purposes.

Radiotherapy treatment planning (also referred to herein as radiation treatment planning) is a complex and patient specific optimization problem. Given the anatomy of the patient, e.g., as illustrated in medical images of the patient, identifications or masks of the PTV and the OARs and the clinical objectives set by physicians, the ultimate goal is to determine a treatment plan that satisfies the clinical objectives. However, the radiation treatment planning problem is usually formulated as an optimization problem with a cost function (also referred to herein as an objective function) defined in terms of one or more optimization objectives. The optimization objectives can be related to, but are usually different from, the clinical objectives set by physicians. It is usually mathematically difficult to accurately incorporate or formulate the clinical objectives into the objective function. Instead, some of the optimization objectives, or terms thereof, can be viewed as distorted representations of the clinical objectives. As such, a radiotherapy treatment plan (also referred to herein as a radiation treatment plan) obtained by solving the optimization problem would usually satisfy the optimization objectives, but not necessarily the clinical objectives. This calls for modifying the optimization objectives to drive the radiotherapy plan towards meeting the clinical objectives and clinical plan improvements as perceived by the physician.

To address, the discrepancy or mismatch between the optimization objectives represented in the objective function and the clinical objectives set by physicians, a quality score or a quality score function can be used to assess the quality of the radiation treatment plan with respect to how well the radiation treatment plan produced by the optimization of the objective function satisfies or meets the clinical objectives. However, using the quality score function to improve the quality of the radiation treatment plan poses serious technical challenges. A first technical challenge is how to use the quality score function to improve the quality of the radiotherapy treatment plan produced by the optimization of the objective function. Specifically, how the quality score function can be used to efficiently and reliably modify the objective function in a way to increase or maximize the quality score of the radiotherapy treatment plan produced by the modified objective function.

Another technical problem is how to define or formulate the quality score function based on or using the clinical objectives. The clinical objectives are typically defined at discrete points. In contrast, the quality score function is desired to be a continuous function in order to allow for computing or estimating the Jacobian of the quality score function with respect to parameters of objective function. Furthermore, the relative importance and/or priorities of the various clinical objectives are to be taken into consideration when formulating the quality score function, which adds to the complexity and/or technical challenge in defining the quality score function.

In the current disclosure, a general framework for adjusting or modifying the objective function for an automated radiotherapy treatment planning system is described. Systems and methods described herein employ a quality score function (also referred to herein as plan quality score function) $S(\overline{q})$ to automatically adjust or modify the objective function (or cost function C) and/or related optimization objectives used by an objective function optimization engine to determine a radiotherapy treatment plan. The optimization objectives can be related to dose-volume histogram (DVH) constraints or can defined based directly on fluence F (e.g., smoothness of the fluence). The optimization objectives can be viewed as controlling variables of the objective function, which define or relate to parameters of the radiation treatment plan P, the fluence F and/or the radiation dose distribution D). The plan quality score function) $S(\overline{q})$ can be used to adjust or modify constant parameters (e.g., parameters other than the variables) of the objective function (or cost function) C, which is to be minimized (e.g., by an objective function optimization engine) to determine an adequate radiation treatment plan.

Embodiments described herein also relate to systems and methods for generating or providing quality score functions for use to improve radiotherapy treatment planning. Given a set of discrete clinical objectives, the systems and methods described herein can generate a continuous quality score function using the discrete clinical objectives. The quality score function takes into account the relative priorities and importance of the various clinical objectives.

For purposes of reading the description of the various embodiments below, the following descriptions of the sections of the specification and their respective contents may be helpful:

- Section A describes a computing and network environment for radiation treatment planning which may be useful for practicing embodiments described herein.
- Section B describes systems and methods for optimizing radiation treatment plans based on a plan quality score function.
- Section C describes systems and methods for generating quality score functions for radiation treatment planning.

A. Computing and Network Environment for Radiation Treatment Planning

FIG. 1A illustrates an example computer environment 100 that can be used to provide a network-based implementation of the methods described herein. The computer environment 100 can include a radiotherapy planning system 110 (also referred to herein as radiation treatment system 110), a user computing device 120 and electronic data sources 130_a-e_ (referred to collectively as electronic data source 130). The radiotherapy planning system 110 can include one or more computer servers 110_a_ (or more generally one or more computing devices 110_a_) and one or more databases 110_b_. The above-mentioned components may be connected to each other through a network 140. The examples of the network 140 may include, but are not limited to, private or public LAN, WLAN, MAN, WAN, and the Internet. The network 140 may include both wired and wireless communications according to one or more standards and/or via one or more transport mediums.

The communication over the network 140 may be performed in accordance with various communication protocols such as Transmission Control Protocol and Internet Protocol (TCP/IP), User Datagram Protocol (UDP), and IEEE communication protocols. In one example, the network 140 may include wireless communications according to Bluetooth specification sets or another standard or proprietary wireless communication protocol. In another example, the network 140 may also include communications over a cellular network, including, e.g., a GSM (Global System for Mobile Communications), CDMA (Code Division Multiple Access), EDGE (Enhanced Data for Global Evolution) network.

The computer environment 100 is not necessarily confined to the components described herein and may include additional or alternate components, not shown for brevity, which are to be considered within the scope of the embodiments described herein.

In some implementations, the computer server 110*a* can be configured to execute computer instructions to perform any of the methods described herein or operations thereof. The computer server(s) 110*a* may generate and display an electronic platform to display information indicative of, or related to, parameters of a radiation treatment plan and/or parameter values related to the quality score function S(q). The electronic platform may include graphical user interface (GUI) displayed on the user computing device 120. An example of the electronic platform generated and hosted by the computer server(s) 110*a* may be a web-based application or a website configured to be displayed on different electronic devices, such as mobile devices, tablets, personal computer, and the like (e.g., user computing device 120).

The computer server(s) 110*a* may host a website accessible to end-users, where the content presented via the various webpages may be controlled based upon each particular user's role or viewing permissions. The computer server(s) 110*a* may be any computing device comprising a processor and non-transitory machine-readable storage capable of executing the various tasks and processes described herein. Non-limiting examples of such computing devices may include workstation computers, laptop computers, server computers, laptop computers, and the like. While the computer environment 100 in FIG. 1A includes a single computer server 110*a*, in some configurations, the radiotherapy planning system 110 may include any number of computing devices, e.g., operating in a distributed computing environment.

The computer server(s) 110*a* may execute software applications configured to display the electronic platform (e.g., host a website), which may generate and serve various webpages to each user computing device 120. Different users operating the user computing device(s) 120 may use the website to view and/or interact with the output radiation treatment plans or parameters values of the quality score function S(q).

In some implementations, the computer server 110*a* may be configured to require user authentication based upon a set of user authorization credentials (e.g., username, password, biometrics, cryptographic certificate, and the like). In such implementations, the computer server(s) 110*a* may access the system database(s) 110*b* configured to store user credentials, which the computer server(s) 110*a* may be configured to reference in order to determine whether a set of entered credentials (purportedly authenticating the user) match an appropriate set of credentials that identify and authenticate the user.

In some configurations, the computer server(s) 110*a* may generate and host webpages based upon a particular user's role (e.g., administrator, employee, and/or bidder). In such implementations, the user's role may be defined by data fields and input fields in user records stored in the system database(s) 110*b*. The computer server(s) 110*a* may authenticate the user and may identify the user's role by executing an access directory protocol (e.g. LDAP). The computer server(s) 110*a* may generate webpage content that is customized according to the user's role defined by the user record in the system database(s) 110*b*.

In some embodiments, the computer server(s) 110*a* receives medical images, masks and/or medical data indicative of medical goals from a user (or retrieve from a data repository), process the data, and displays an indication of the treatment trajectory on the electronic platform. For instance, in a non-limiting example, a user operating the computing device 130*a* uploads a series of images of a CT scan or other medical images using the electronic platform. The computer server(s) 110*a* can determine the treatment trajectory based on input data, and display the results via the electronic platform on the user computing device 120 or the computing device 130*a*. The user computing device 120 and/or the computing device 130*a* may be any computing device comprising a processor and a non-transitory machine-readable storage medium capable of performing the various tasks and processes described herein. Non-limiting examples of a network node may be a workstation computer, laptop computer, tablet computer, and server computer. In operation, various users may use user computing devices 120 and or computing device 130*a* to access the GUI operationally managed by the computer server(s) 110*a*.

The electronic data sources 130 may represent various electronic data sources that contain and/or retrieve medical images of patients. For instance, database 130*b* and third-party server 130*c* may represent data sources providing the corpus of data (e.g., medical images, masks or other medical data) needed for the computer server(s) 110*a* to determine radiation treatment plans. The computer server(s) 110*a* may also retrieve the data directly from a medical scanner 130*e* and/or medical imaging device 130*d* (e.g., CT scan machine).

In some implementations, the methods described herein or operations thereof can be implemented by the user device 120, any of the electronic devices 130 or a combination thereof.

While FIG. 1A shows a network based implementation, it is to be noted that methods described herein can be implemented by a single computing device that receives the medical images and medical data for a patient and determines a radiation treatment trajectory or path according to methods described herein.

Figure 1B:
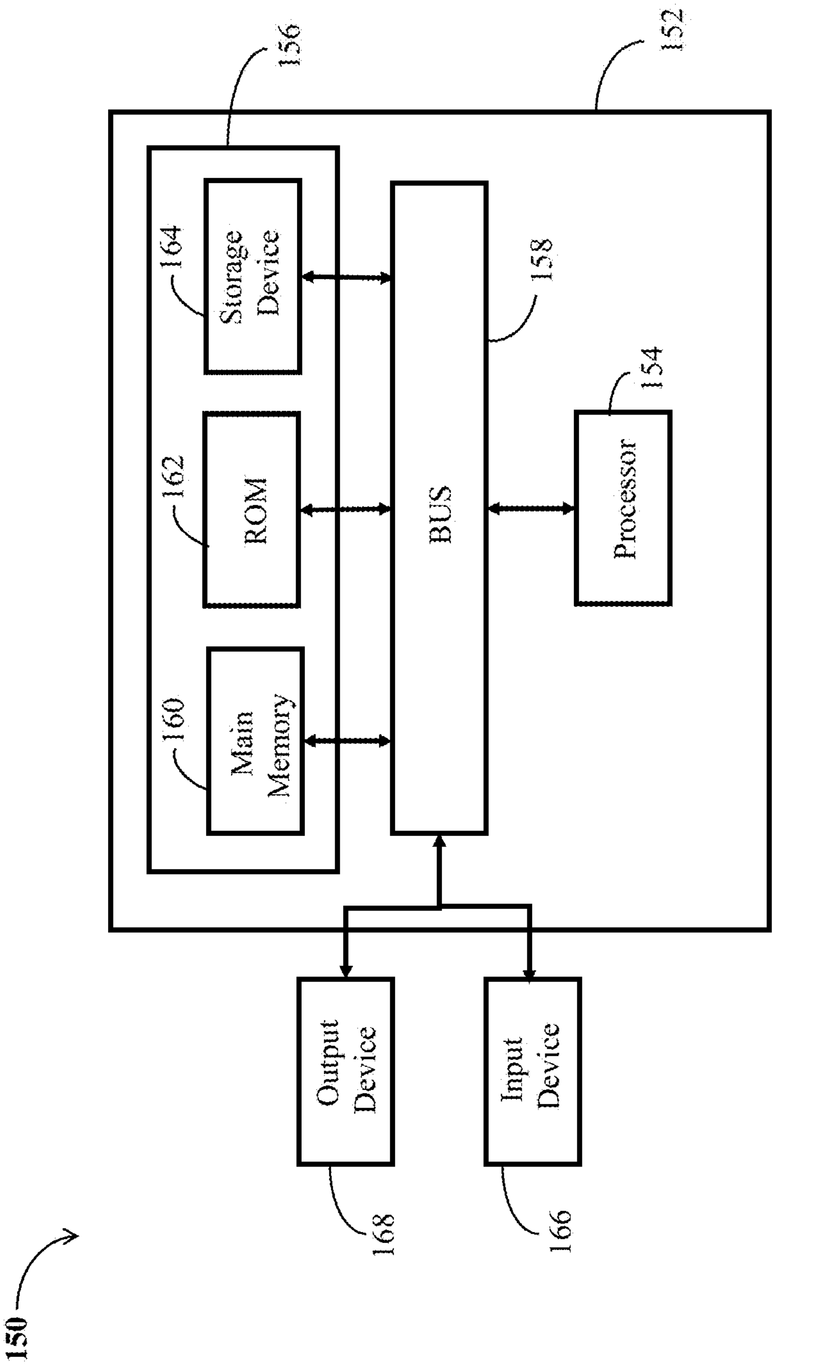
FIG. 1B is a block diagram depicting one implementation of a system architecture, according to an embodiment.

Referring to FIG. 1B, a block diagram depicting one implementation of a system architecture for a computing system 150 that may be employed to implement methods described herein is shown, according to an embodiment. The computing system 150 can include a computing device 152. The computing device 152 can represent an example implementation of any of the devices 110*a*, 120 and/or 130*a-e* of FIG. 1A. For instance, the computing device 152 can include, but is not limited to, a computed tomography (CT) scanner, a medical linear accelerator device, a desktop, a laptop, a hardware computer server, a workstation, a personal digital assistant, a mobile computing device, a smart phone, a tablet, or other type of computing device. The computing device 152 can include a one or more processors 154 to execute computer code instructions, a memory 156 and a bus 158 communicatively coupling the processor 154 and the memory 156.

The one or more processors 154 can include a microprocessor, a general purpose processor, a multi-core processor, a digital signal processor (DSP) or a field programmable gate array (FPGA), an application-specific integrated circuit (ASIC) or other type of processor. The one or more processors 154 can be communicatively coupled to the bus 158 for processing information. The memory 156 can include a main memory device 160, such as a random-access memory (RAM) or other dynamic storage device, coupled to the bus 158 for storing information and instructions to be executed by the processor(s) 154. The main memory device 160 can be used for storing temporary variables or other intermediate information during execution of instructions (e.g., related to methods described herein such as method 300) by the processor(s) 154. The computing device 152 can include a read-only memory (ROM) 162 or other static storage device coupled to the bus 158 for storing static information and instructions for the processor(s) 154. For instance, the ROM 162 can store medical images or other medical data of patients, for example, received as input. The ROM 162 can store computer code instructions related to, or representing an implementation of, methods described herein. A storage device 164, such as a solid state device, magnetic disk or optical disk, can be coupled to the bus 158 for storing (or providing as input) information and/or instructions.

The computing device 152 can be communicatively coupled to, or can include, an input device 166 and/or an output device 168. The computing device 102 can be coupled via the bus 158 to the output device 168. The output device 168 can include a display device, such as a Liquid Crystal Display (LCD), Thin-Film-Transistor LCD (TFT), an Organic Light Emitting Diode (OLED) display, LED display, Electronic Paper display, Plasma Display Panel (PDP), or other display, etc., for displaying information to a user. The output device 168 can include a communication interface for communicating information to other external devices. An input device 166, such as a keyboard including alphanumeric and other keys, may be coupled to the bus 158 for communicating information and command selections to the processor 154. In some implementations, the input device 166 may be integrated within a display device, such as in a touch screen display. The input device 166 can include a cursor control, such as a mouse, a trackball, or cursor direction keys, for communicating direction information and command selections to the processor 154 and for controlling cursor movement on the display device.

According to various implementations, the methods described herein or respective operations can be implemented as an arrangement of computer code instructions that are executed by the processor(s) 154 of the computing system 150. The arrangement of computer code instructions can be read into main memory device 160 from another computer-readable medium, such as the ROM 162 or the storage device 164. Execution of the arrangement of computer code instructions stored in main memory device 160 can cause the computing system 150 to perform the methods described herein or operations thereof. In some implementations, one or more processors 154 in a multi-processor arrangement may be employed to execute the computer code instructions representing an implementation of methods or processes described herein. In some other implementations, hard-wired circuitry may be used in place of or in combination with software instructions to effect illustrative implementation of the methods described herein or operations thereof. In general, implementations are not limited to any specific combination of hardware circuitry and software. The functional operations described in this specification can be implemented in other types of digital electronic circuitry, in computer software, firmware, hardware or a combination thereof.

In some implementations, the computing system 150 can include a plurality of computing devices 152, e.g., operating in a distributed computing environment. The computing system 150 can represent an example implementation of the radiotherapy planning system 110.

B. Optimizing Radiation Treatment Plans Based on Plan Quality Scores

A typical radiotherapy treatment planning system can include an objective function optimization engine configured to optimize (e.g., minimize) an objective function C(P), where P is the radiotherapy treatment plan defined by machine control point properties. The objective function can be defined in terms of the fluence F produced (or expected to be produced) by the radiotherapy treatment plan P as C(F). The objective function can be defined, e.g., by a planner, using a list of N optimization objectives, such as $$C = \sum_{j=1}^{N} c_j(P),$$

where N is an integer and each term $c_j(P)$ represents a separate optimization objective. Some of the optimization objectives can relate directly to the plan or fluence while others can be related to the radiation dose distribution D to be applied to the patient according to the radiation treatment plan P so that $c_j(P)=c_j(D(P))$. An optimization objective can be defined based on dose and volume constraints in a dose-volume histogram (DVH) space. For example, one of these DVH-constraints (or DVH-objectives) could be for the planning target volume (PTV) and can specify that PTV: D95%>50 Gy. This constraint means that the radiation dose to be applied to 95% of PTV volume should be greater than 50 Gy. This constraint can be a clinical constraint defined or set by a physician, and at least one term $c_j(D)$ of the objective function C(P) can be defined based on this clinical constraint in order to have the radiation dose associated with the radiation treatment plan P satisfy this clinical constraint as much as possible. A weight $w_j$ can be assigned for each optimization objective term $c_j(D)$ to scale the cost of the term. For instance, the weight $w_j$ can reflect the priority or importance of the corresponding optimization objective defined by $c_j(D)$. The objective function can have a list of N optimization objectives associated with a weight vector $\overline{w} \in \mathbb{R}^N$. The objective function optimization engine in the radiation treatment planning system can determine a radiation treatment plan P by optimizing the objective function C(P) (e.g., minimizing or maximizing C(P) depending on how C(P) is defined).

A physician (e.g., an oncologist or a radiologist) can defined a set of clinical objectives (e.g., as a set of constraints) to be achieved by the radiation treatment plan. DVH-constraints, or other forms of clinical objectives, may not be accurately or exactly implemented into the objective function C(P). For example, the clinical constraint that PTV: D95%>50 Gy cannot be accurately represented or integrated in the objective function C(P). Instead, an optimization objective (e.g., defined by the optimization objective term $c_j(D)$) that is different from, but related to, the clinical objective is usually used. Given the difference between the clinical objective and the corresponding optimization objective, optimizing the objective function does not guarantee that the resulting plan P will satisfy the clinical objective. Furthermore, the objective function and the optimization objective terms $c_j(D)$ depend substantially on the patient geometry or patient anatomy, and they cannot be used as standard metrics for evaluating the quality of the radiation treatment plan produced by the optimization process. For example, for two different patients, using the same set of optimization objectives with the same weights would not generally result in a good plan for both patients. Instead, the planner has to customize the optimization objectives and the corresponding weights for each patient during the planning process.

A quality score function $S(\overline{q})$ can be used to assess the quality of a radiation treatment plan P produced by the optimization of the objective function C(P), where the vector $\overline{q}=(q_1, q_2, \ldots, q_M)$ is a vector of M quality metrics or a vector of M quality values achieved by (or associated with) the radiation treatment plan P. The quality score function $S(\overline{q})$ can be a function defined as discussed in Section C or otherwise defined differently. The quality score function $S(\overline{q})$ is usually different from the objective function, and the quality metrics (or quality values) $q_1, q_2, \ldots, q_M$ and/or corresponding constraints representing the clinical objectives are typically different from the optimization objective terms $c_1(D), c_2(D), \ldots, c_N(D)$. For instance, a constraint associated with a quality metric (or quality value) $q_i$ may not be accurately represented by any of the optimization objective terms $c_j(D)$. Each quality metric (or quality value) $q_i$ can depend on the radiotherapy treatment plan P, the fluence F and/or the radiation dose distribution D. In some implementations, all the M quality metrics (or quality values) $q_1, q_2, \ldots, q_M$ can be related to clinical objectives (or clinical goals) set by the physician(s) or other medical personnel. For example, the value of each $q_i$ can represent an achieved value of a metric defined by a corresponding clinical objective. In some implementations, the quality metrics (or quality values) can include one or more quality metrics or values defined by other objectives, e.g., other than clinical objectives. In some implementations, the quality score function may not include all desired objectives. For example, some quality aspects of the radiation treatment plan can be controlled by the objective function or an optimization objective term thereof, but not by the quality score function or any quality metric thereof. For instance, leaf-movement objectives or constraints that are easy to control via the objective function may not be represented within the quality score function $S(\overline{q})$.

Table 1 below illustrates six example clinical objectives. For a certain radiation treatment plan, each of these clinical objectives has, or is associated with, a corresponding $q_i$ value that is achieved (or to be achieved). The set of quality metrics (or quality values) $q_i$ can be represented as a vector $\overline{q}$. The quality metric score, or the value of the quality score function $S(\overline{q})$ can be calculated. The exact formulation of the plan quality score function can depend on the relative priorities and relative importance of the different clinical objectives.

TABLE 1

| Clinical Objectives/Goals | |
|---|---|
| Lt Parotid | (P1.1) D50.0% ≤ 20.00 Gy |
| Rt Parotid | (P1.2) D50.0% ≤ 20.00 Gy |
| PTV | (P2.1) D90.0% ≥ 50.00 Gy |
| PTV | (P2.2) D99.0% ≥ 46.50 Gy |

TABLE 1-continued

| Clinical Objectives/Goals | |
|---|---|
| PTV | (P2.3) D20.0% < 55.00 Gy |
| Cord | (P2.4) Dmax (0.0%) < 40.00 Gy |

The clinical objective P1.1 is specific to the left parotid gland, and specifies that the radiation dose for no more than 50% of the volume of the left parotid gland should exceed 20.00 Gy. The clinical objective P1.2 is specific to the right parotid gland, and specifies that the radiation dose for no more than 50% of the volume of the right parotid gland should exceed 20.00. The clinical objective P2.1 is specific to the PTV, and specifies that the radiation dose for 90% of the volume of the PTV should be greater than or equal to 50.00 Gy. The clinical objective P2.2 is specific to the PTV, and specifies that the radiation dose for 99% of the volume of the PTV should be greater than or equal to 46.50 Gy. The clinical objective P2.3 is specific to the PTV, and specifies that the radiation dose for no more than 20% of the volume of the PTV should exceed 55.00 Gy. The clinical objective P2.4 is specific to the spinal cord, and specifies that the maximum radiation dose for the spinal cord should be less than 40.00 Gy.

The quality score function $S(\overline{q})$ can be formulated or defined to represent the clinical objectives (e.g., objectives P1.1, P1.2, P2.1, P2.2, P2.3 and P2.4) set by the physician (s). By maximizing the plan quality score $S(\overline{q})$ one can ensure that the corresponding radiotherapy treatment plan satisfies or meets the clinical objective, at least up to some desired extent. As such, improving the quality of the radiotherapy treatment plan can be achieved by determining a radiotherapy treatment plan that maximizes the plan quality score $S(\overline{q})$ or leads to a plan quality score $S(\overline{q})$ that is greater than a predefined score threshold.

The maximization of the quality score function $S(\overline{q})$ introduces various technical problems or challenges. Embodiments described herein allow for automatically determining a good quality radiotherapy treatment plan for a patient, e.g., with a relatively high quality score $S(\overline{q})$. This can be achieved by optimizing the objective function C to determine a radiotherapy treatment plan P, evaluating the quality score function for the radiotherapy treatment plan P, and adjusting one or more parameters of the objective function C (e.g., to determine a new or modified objective function) so that a new radiotherapy plan produced by the new/modified objective function results in a higher quality score $S(\overline{q})$ than the previous radiotherapy treatment plan P. Adjusting the one or more parameters of the objective function C in a way to increase or maximize the quality score $S(\overline{q})$ calls for determining or calculating a change in $S(\overline{q})$ as a function of constant parameters of the objective function to be adjusted. The constant parameters of the objective function can include the objective positions $(\overline{d}, \overline{v}, \overline{w})$, where the vectors $\overline{d}$ and $\overline{v}$ represent locations and volumes of regions specific to various optimization objectives in the dose-volume space and the vector $\overline{w}$ represents objective weights of the optimization objectives or the corresponding optimization objective terms $c_j(\cdot)$ for $j=1, \ldots, N$.

In this context the analytical calculation of the change in $S(\overline{q})$ as a function of the parameters of the objective function C may not be mathematically feasible or practical. Considering the objective weights $\overline{w}$, for example, the chain rule implies that $$\frac{\delta S}{\delta \overline{w}} = \frac{\delta S}{\delta \overline{q}} \frac{\delta \overline{q}}{\delta \overline{w}}.$$

While the quality score function $S(\overline{q})$ can be chosen so that $$\frac{\delta S}{\delta \overline{q}}$$

can be accurately calculated, the analytical form of the Jacobian $$\frac{\delta \overline{q}}{\delta \overline{w}}$$

is not known or may not be easily determined. The relationship between the quality metrics in the quality metric vector $\overline{q}$ and the optimization objective weights in the weight vector $\overline{w}$ is very complicated given the dependency on patient geometry, field setup, objective placement, and the interaction between various optimization objectives. The same is usually true for $\overline{d}$, $\overline{v}$ and/or other constant parameters of the objective function C. Hence, a direct gradient approach may not be feasible or utilized to determine how the parameters of the objective function C are to be adjusted or modified to maximize or increase the plan quality score $S(\overline{q})$.

Embodiments described herein, allow for estimating the Jacobian $$\frac{\delta \overline{q}}{\delta \overline{w}},$$

and use the estimate of the Jacobian to determine adjustments or changes to the parameters of the objective function C that would lead to maximizing or increasing the plan quality score $S(\overline{q})$. For instance, the plan quality optimization engine 208 or the objective function updating component 214 shown in FIG. 2 can estimate entries of the Jacobian $$\frac{\delta \overline{q}}{\delta \overline{w}}$$

and determine for each parameter of objective function to be adjusted a corresponding adjustment using some of the entries of the Jacobian $$\frac{\delta \overline{q}}{\delta \overline{w}}.$$

Figure 2:
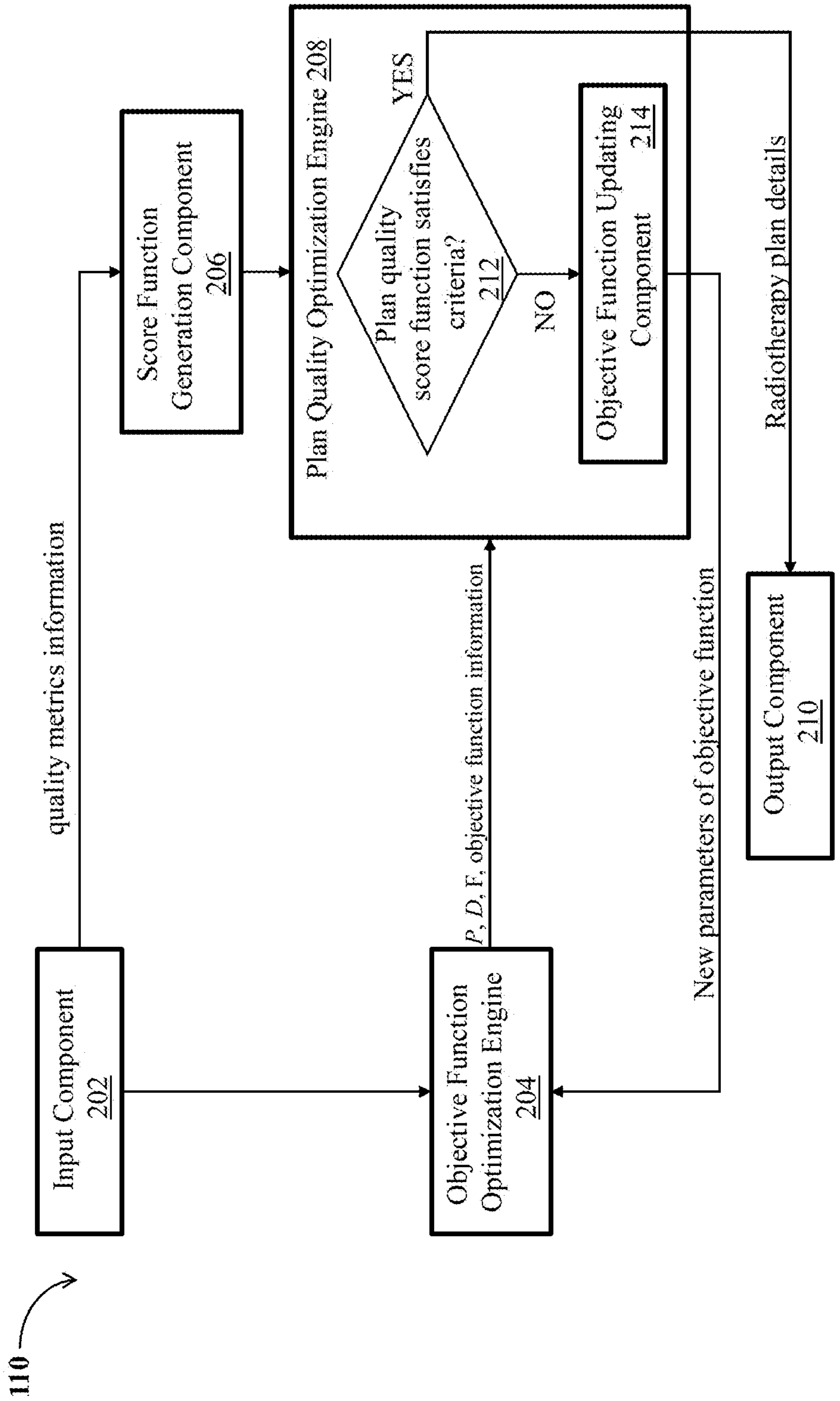
FIG. 2 is a block diagram of a radiotherapy treatment planning system, according to an embodiment.

Referring now to FIG. 2, a block diagram of the radiotherapy planning system 110 is shown, according to example embodiments. In brief overview, the radiotherapy planning system 110 can include an input component 202, an objective function optimization engine 204, a score function generation component 206, a plan quality optimization engine 208 and an output component 210. The plan quality optimization engine 208 can a decision block (or comparator) 212 to determine whether the quality score function $S(\overline{q})$ satisfies one or more criteria, and an objective function updating component 214. Each of the components 202, 204, 206, 208, 210, 212 and 214 can be implemented as software, firmware, hardware or a combination thereof. For instance, any of the components 202, 204, 206, 208, 210, 212 and 214 can be implemented as executable instructions that are executed by the processor(s) 154.

The input component 202 can receive input data from the data source 130 and/or the user computing device 120. The input component 202 can receive, from the data source 130, medical images and/or other data of the patient for whom a radiotherapy plan is to be prepared. The input component 202 can receive information related to the objective function C(P) and/or information related to the quality score function $S(\overline{q})$ from the computing device 120 or the input device 166. The information related to the objective function C(P) can include values of the weight vector $\overline{w}$, other parameters of the objective function and/or descriptions or parameters of the clinical objectives. The information related to the quality score function $S(\overline{q})$ can include the descriptions or parameters of the clinical objectives, parameters or descriptions of the quality metrics (or quality values) $q_i$, priorities of the clinical objectives, weights associated with the quality metrics or a combination thereof. The input component 202 can provide the medical images, other patient data and/or the information related to the objective function to the objective function optimization engine 204. The input component 202 can provide the information related to the quality score function to the plan quality optimization engine 208.

The objective function optimization engine 204 can receive input data from the input component, and iteratively optimize (or run optimization of) the objective function C(P) for one or more iterations. As used herein, iteratively optimizing the objective function for one or more iterations means iteratively updating parameters of the radiotherapy plan P to minimize (or alternatively maximize) the objective function. For instance, the objective function optimization engine 204 can iteratively update parameters of radiation beams, e.g., by iteratively updating parameters of a multi leaf collimator (MLC) or radiation angles, to iteratively decrease (or increase) the objective function. Note that depending on how the objective function C(P) is defined, the goal of the objective function optimization can be either minimizing or maximizing the objective function.

In some implementations, the objective function optimization engine 204 can iteratively optimize the objective function C(P) until a predefined convergence is achieved. For instance, in the case of minimizing the objective function, the predefined convergence can be defined as the value of the objective function C(P) becoming smaller than a predefined threshold value, or the value of the objective function C(P) decreasing by a predefined amount. In some implementations, the objective function optimization engine 204 can iteratively optimize the objective function C(P) for a predefined number of iterations. When the optimization of the objective function is complete, the objective function optimization engine 204 can provide information related to (e.g., parameters of) the objective function C(P) and/or information related to (e.g., parameters of) the radiotherapy plan P to the plan quality optimization engine 208. The objective function optimization engine 204 may further provide quality metrics information to the plan quality optimization engine 208.

The score function generation component 206 can receive indications of the clinical objectives and generate a plan quality score function for use to assess and improve the quality of the radiotherapy treatment plans generated by the objective function optimization component 204. In some implementations, and with regard to the optimization of the radiotherapy treatment plan optimization, the plan quality score function (or quality score function) can be provided as input, in which case the score function generation component 206 can be optional or omitted. The score function generation component 206 is described in further detail in section C below.

The plan quality optimization engine 208 can use the received quality metrics information, the objective function information and/or the radiotherapy plan information to adjust one or more parameters of the objective function C(P). The plan quality optimization engine 208 can use the received information to evaluate or compute a quality score of the radiotherapy plan P. The decision block 212 can determine whether the quality score or the quality score function $S(\overline{q})$ satisfies one or more predefined criteria. If the quality score function $S(\overline{q})$ satisfies the one or more criteria, the plan quality optimization engine 208 can provide details of the radiotherapy plan P to the output component 210. Otherwise, the plan quality optimization engine 208 can update or adjust the one or more parameters of the objective function C(P) in a way to improve (e.g., increase or maximize) the quality score defined by the quality score function $S(\overline{q})$. Updating parameters of the objective function C(P) can include updating or adjusting the weight vector $\overline{w}$ and/or other parameters of the objective function C(P). Details of updating or adjusting the parameters of the objective function C(P) are discussed in further detail below with regard to FIG. 3. The plan quality optimization engine 208 can provide the updated parameters of the objective function C(P) to the objective function optimization engine 204. The objective function optimization engine 204 can optimize the new objective function as defined by the updated parameters for one or more iterations, and provide information related to the new objective function C(P) and/or information related to (e.g., parameters of) the new radiotherapy plan P (produced by optimizing new objective function) to the plan quality optimization engine 208. The loop between the objective function optimization engine 204 and the plan quality optimization engine 208 can be repeated until the quality score function $S(\overline{q})$ is determined to satisfy the one or more criteria, in which case the plan quality optimization engine 208 can provide the details of the latest radiotherapy plan P to the output component 210.

The output component 210 can display information related to or defining the radiotherapy plan P, e.g., on display device 168, to the planner. The output component 210 can store the information related to or defining the radiotherapy plan P in the database **110*b* for access at a later time, e.g., by the user computing device 120, or transmit the information to an external device (e.g., the user computing device 120). The output component 210 may further receive the quality score or other values associated with the quality score function $S(\overline{q})$ from the plan quality optimization engine 208. The output component 210 can display the value(s) associated with the quality score function $S(\overline{q})$, store such values in the database 110*b*, or provide the values to an external device (e.g., user computing device 120**).

Figure 3:
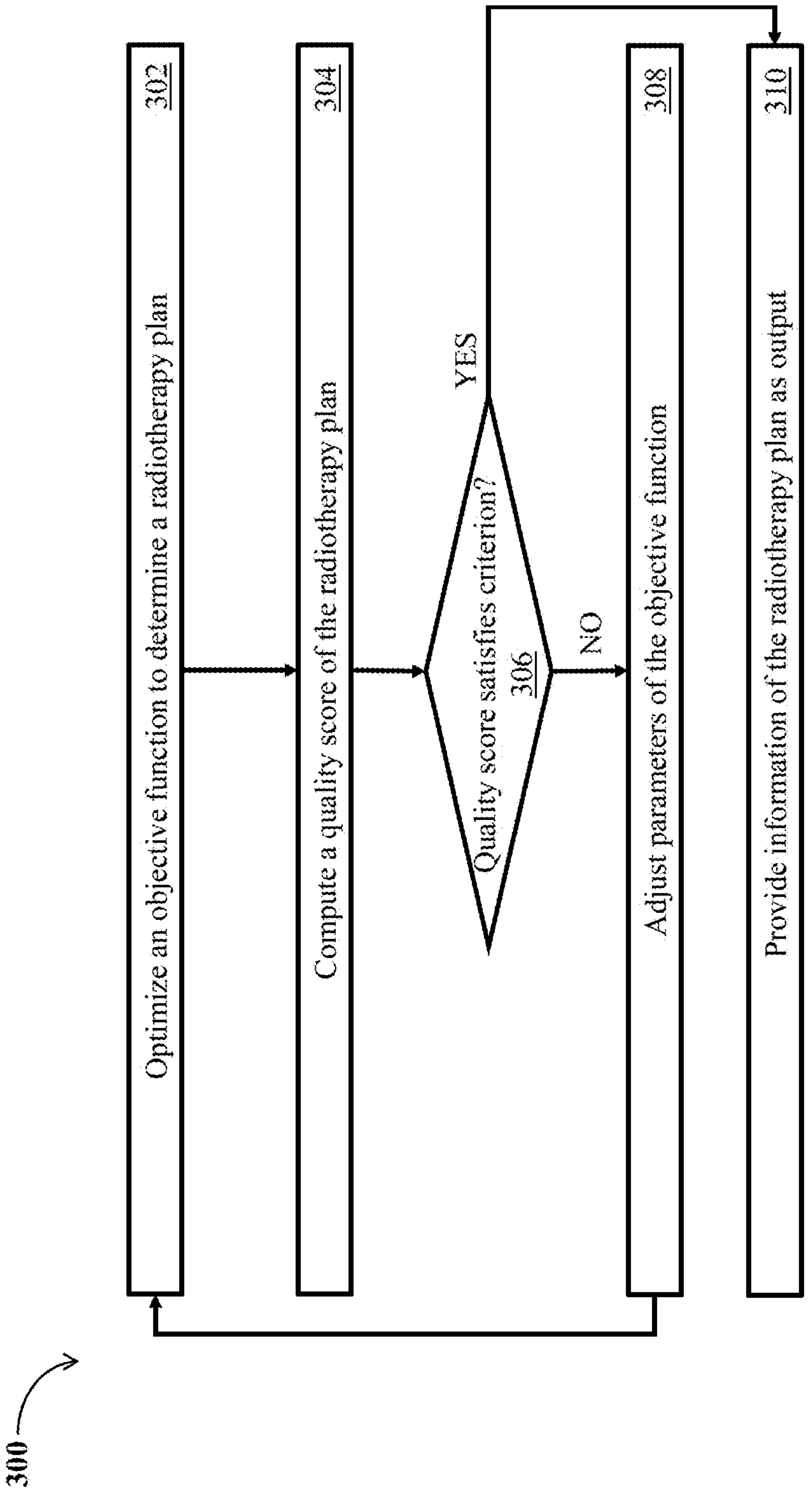
FIG. 3 is a flowchart illustrating a method of radiation treatment planning, according to an embodiment.

FIG. 3 shows a flowchart illustrating an embodiment of a method 300 of radiation treatment planning, according to inventive concepts of this disclosure. In brief overview, the method 300 can include the computing system 150 or the processor(s) 154 iteratively optimizing an objective function for one or more iterations to determine a radiotherapy plan (STEP 302), and computing or determining a quality score of the radiotherapy plan (STEP 304). The method 300 can include the computing system 150 or the processor(s) 154 determining whether the quality score or the corresponding quality score function satisfies one or more criteria (DECISION BLOCK 306). Upon determining that the quality score or the corresponding quality score function does not satisfy the one or more criteria, the computing system 150 or the processor(s) 154 can adjust parameters of the objective function (STEP 308), otherwise provide information of the radiotherapy plan as out output (STEP 310).

The method 300 can include the computing system 150 or the processor(s) 154 optimizing an objective function to determine a radiotherapy plan (STEP 302). The computing system 150 or the processor(s) 154 can receive patient data indicative of an anatomical region of the patient, the PTV and other organs in the anatomical region, prescribed radiation dose, clinical objectives specific to the patient, other patient medical information, non-medical patient information. The computing system 150 or the processor(s) 154 can receive the patient data from the electronic data source 103, the user computing device 120 and/or other input means. The patient data can include medical images of the anatomical region and/or one or more masks indicative of the PTV and organs within the anatomical region. The medical images can include three-dimensional (3-D) images, two-dimensional (2-D) images, computer tomography (CT) images, magnetic resonance (MR) images, medical images produced by other medical imaging modalities or a combination thereof. The computing system 150 or the processor (s) 154 can receive information indicative of a formulation of the objective function C(P) and/or initial values of the parameters of the objective function C(P). In some implementations, the computing system 150 or the processor(s) 154 can set the initial values of the parameters of the objective function C(P).

In determining the radiotherapy plan, the computing system 150 or the processor(s) 154 can perform a single-step optimization or an iterative optimization of the objective function C(P) determine one or more plan parameters defining the radiotherapy plan. The parameters of the radiotherapy plan can include MLC control parameters, radiation angles, radiation intensity values or a combination thereof. The computing system 150 or the processor(s) 154 can optimize the objective function C(P) for one or more iterations until some predefined criterion is met. For example, the criterion can include a value of the objective function C(P) being less than a predefined threshold and/or a predefined number of iterations has been reached. During the iterative optimization, the computing system 150 or the processor(s) 154 can iteratively update the one or more parameters of the radiotherapy plan in a way to iteratively decrease (or increase) the objective function value.

The objective function can be defined in terms of one or more optimization objectives related to the one or more parameters of the radiotherapy plan, the fluence matrix F, the dose distribution D, the radiotherapy plan P or a combination thereof. For instance, the objective function can be defined as $$C(P, F, D) = \sum_{j=1}^{N} w_j c_j(P, F, D),$$

where each term $c_j(P, F, D)$ corresponds to a separate optimization objective and each parameter $w_j$ represents a weighting of the optimization objective term $c_j(P, F, D)$. The weighting parameters $w_j$ form the weight vector $\overline{w} \in \mathbb{R}^N$. At least some of the optimization objectives corresponding to some of the terms $c_j(P, F, D)$ can related to, but different from, the clinical objectives set by the physician(s). For instance, some of the optimization objectives can correspond to the clinical objectives associated with the quality metrics $q_1, q_2, \ldots, q_M$, while other optimization objective may represent objectives related to the radiation machine or other optimization objectives.

Each optimization objective or corresponding optimization objective term $c_j(P, F, D)$ can be associated with a respective specific region in the dose-volume space, e.g., defined by a respective position and respective volume $(d_j, v_j)$ in the dose-volume space. For instance, some optimization objectives can be specific to PTV while others can be specific to one or more organs-at-risk (OARs). The position and volume $(d_j, v_i)$ for each optimization objective or corresponding optimization objective term $c_j(P, F, D)$ can be constant.

As discussed above with regard to FIG. 2, the optimization of the objective function C(P, F, D) can be performed by the objective function optimization engine 204. The radiotherapy plan P produced by the optimization of the objective function C(P, F, D) may not necessarily satisfy (at least to some desired extent) the clinical objectives set by the physicians. Accordingly, the objective function optimization engine 204 can provide the produced radiotherapy plan P to the plan quality optimization engine 208 for assessing the quality of the plan. The objective function optimization engine 204 can provide other information, such as the radiation dose distribution D associated with the radiotherapy plan P, the fluence matrix/associated with the radiotherapy plan P, information related to the objective function C(P, F, D) (e.g., values of the optimization objective terms $c_j(P, F, D)$) or a combination thereof.

The method 300 can include the computing system 150 or the processor(s) 154 computing or determining a quality score of the radiotherapy plan (STEP 304). The computing system 150 or the processor(s) 154 can compute the quality score of the radiotherapy plan using the parameters P, D) and/or F associated with the radiotherapy plan produced as a result of the optimization of the objective function C(P, F, D). The computing system 150 or the processor(s) 154 can compute the quality score of the radiotherapy plan by evaluating the quality score function $S(\overline{q})$ using the parameters P, D and/or F.

The plan quality optimization engine 208 can evaluate each of the quality metrics $q_1, q_2, \ldots, q_M$ using the parameters P, D and/or F received from the objective function optimization engine 204. Each (or at least one) quality metric $q_i$ can be associated with a corresponding clinical objective. The clinical objective can be related to a corresponding optimization objective or a corresponding optimization objective term $c_j(P, F, D)$. The clinical objective and the corresponding optimization objective can be defined, for example, within a specific region in the dose-volume space, where the specific region can be defined by the constant position and volume $(d_j, v_j)$ in the dose-volume space. For instance, some clinical objectives can be specific to PTV while others can be specific to one or more organs-at-risk (OARs). The plan quality optimization engine 208 can evaluate the quality score function $S(\overline{q})$ using the determined quality metric vector $\overline{q}=(q_1, q_2, \ldots, q_M)$ to determine the quality score of the radiotherapy plan produced by the objective function optimization engine 204. In some implementations, the objective function optimization engine 204 can evaluate the quality metrics and provide the values of the quality metric vector $\overline{q}=(q_1, q_2, \ldots, q_M)$ to the plan quality optimization engine 208.

The general formulation of the quality score function $S(\overline{q})$ can be known to the plan quality optimization engine 208. For example, the general formulation of the quality score function $S(\overline{q})$ can be provided as input or determined by the quality score function generation component 206. In some implementations, the quality score function can be defined as $$S(\overline{q}) = \sum_{i=1}^{M} s_i(q_i),$$

where each $s_i(q_i)$ represents a quality sub-score corresponding to the quality metric $q_i$. The plan quality optimization engine 208 can evaluate each $s_i(q_i)$ and compute the sum (or a weighted sum) of the quality sub-score to determine the value of $S(\overline{q})$.

The method 300 can include the computing system 150 or the processor(s) 154 determining whether the quality score satisfies one or more criteria (DECISION BLOCK 306). For instance, the plan quality optimization engine 208 can compare the value of the quality score function $S(\overline{q})$ to a predefined threshold value. In some implementations, the plan quality optimization engine 208 can compare at least one quality sub-score $s_i(q_i)$ to a corresponding threshold value. For example, if the quality score (value of $S(\overline{q})$) is greater than the corresponding threshold value, the plan quality optimization engine 208 can determine that the radiotherapy plan P is of "good" or "acceptable" quality, otherwise determine that the radiotherapy plan P is of "bad" or "unacceptable" quality. In some implementations, if the quality score (value of $S(\overline{q})$) and/or the quality sub-score(s) $s_i(q_i)$ are greater than the corresponding thresholds, the plan quality optimization engine 208 can determine that the radiotherapy plan P is of "good" or "acceptable" quality, otherwise determine that the radiotherapy plan P is of "bad" or "unacceptable" quality. Based on the comparison or whether the quality score satisfies the one or more criteria, the plan quality optimization engine 208 can determine whether to adjust the parameters of the objective function C(P, F, D) in order to enhance quality or to trigger output of the details of the already produced radiotherapy plan. In some implementations, even if the quality score(s) is/are determined not to satisfy the one or more criteria, the plan quality optimization engine 208 or the decision block 212 can decide not to adjust the parameters of the objective function C(P, F, D) and output the radiotherapy treatment plan, if previous adjustments or iterations did not result in an increase (e.g., an improvement or increase beyond a predefined threshold) in the quality score.

The method 300 can include the computing system 150 or the processor(s) 154 adjusting one or more parameters of the objective function upon determining that the computed quality score does not satisfy the one or more criteria (STEP 308). The plan quality optimization engine 208 can adjust one or more parameters defining the form of the objective function C(P, F, D), upon determining that the radiotherapy plan P is not a "good" or "acceptable" plan. The adjusted parameter(s) can be different from the variables, e.g., P, F and/or D), of the objective function C(P, F, D). In other words, while the objective function optimization engine 204 is configured to determine or adjust the variables, e.g., P, F and/or D), of the objective function C(P, F, D) in a way to minimize (or maximize) the objective function C(P, F, D), the plan quality optimization engine 208 can be configured to determine or adjust other parameters of the objective function C(P, F, D) (e.g., parameters that define the form of the objective function and/or that are different from the variables determined or adjusted by the objective function optimization engine 204) in a way increase or maximize the quality score $S(\overline{q})$ and/or any quality sub-score $s_i(q_i)$.

In some implementations, in adjusting the one or more parameters of the objective function C(P, F, D), the plan quality optimization engine 208 or the objective function updating component 214 can adjust one or more weights $w_j$ of the weight vector $\overline{w}$. For instance, the plan quality optimization engine 208 or the quality optimization engine 208 can adjust the weight vector $\overline{w}$. In some implementations, the quality optimization engine 208 or the objective function updating component 214 can adjust one or more parameters of at least one optimization objective term $c_j$(P, F, D). For example, an optimization objective term can be defined as $c_j(P, F, D)=|f(P, F, D)-\beta_j|^2$, where $f$ (P, F, D) is a function of the variables P, F and/or D) and $\beta_j$ is a constant. The plan quality optimization engine 208 or the objective function updating component 214 can adjust $\beta_j$, for example, in a way to increase or maximize the quality score $S(\overline{q})$ and/or any quality sub-score $s_i(q_i)$. In some implementations, the quality optimization engine 208 or the objective function updating component 214 may adjust the position vector $\overline{d}$ representing positions of the regions specific to optimization objectives, the volume vector $\overline{v}$ representing volumes of the regions specific to optimization objectives, the weighting vector $\overline{w}$, other constant parameters of the objective function C(P, F, D) or a combination thereof.

It is be mentioned here that the plan quality optimization engine 208 or the objective function updating component 214 can also be implemented to adjust parameters associated with a group of optimization objectives instead of handling each of optimization objective individually. In that case any of the N optimization objective terms can represent a group of optimization objectives instead of a single optimization objective. A collection of modified optimization objectives can form a group where only one optimization objective is the so called "main objective" which directly links to some clinical objective metric. In one example, the main objective could be driving the PTV coverage, while a set of "helper" objectives belonging to that group could be helping the PTV DVH to have a preferred shape, which in turn is not directly linked to any goal value. Weighting of the optimization objectives in the group can be manipulated synchronously so that $c_j$ is the sum over all the optimization objectives in the group.

The purpose of the adjustment or modification of the parameters of the objective function is to suggest/determine new parameters (e.g., new weights $w_j$) for the optimization objectives in order to improve the quality score $S(\overline{q})$. Or equivalently to suggest how the parameters (e.g., the weights $w_j$) should be changed for example by suggesting scalers by which the weights should be modified. The new parameters can be viewed as representing a new objective function, and can be provided to the objective function optimization engine 204 to run a new optimization and determine a new radiotherapy treatment plan.

As discussed above, updating the parameters of the objective function to improve the quality score $S(\overline{q})$ calls for determining or estimating the Jacobian of the quality metric vector $\overline{q}$ with respect to the object function parameters (e.g., weighting vector $\overline{w}$). The plan quality optimization engine 208 or the objective function updating component 214 can determine, estimate or construct an approximation of the Jacobian $$A = \frac{\delta \overline{q}}{\delta \overline{w}},$$

and adjust the parameters of the objective function based on the approximation of the Jacobian.

Element or entry $$a_{ij} = \frac{\delta q_i}{\delta w_j}$$

of the Jacobian indicates or gives a prediction of how metric $q_i$ changes when weight $w_j$ is increased. Let one column of the Jacobian be denoted as vector $a_{+j}$. This vector indicates or gives a predicted change to whole $\overline{q}$ responsive to the modification of parameters of a single optimization objective j (e.g., weight $w_j$). Determining of the values $a_{ij}$ is non-trivial. There radiotherapy plan produced by the objective function optimization engine 204 is dependent on the structures or anatomy specific to the patient, the optimization objectives used (which depend on but are usually not exactly similar to the clinical objectives), the field setup, and various other factors. The is no known formulation of the relationship between the quality metrics $q_i$ and the constant objective function parameters that would allow accurate determination of the Jacobian entries $a_{ij}$ beforehand. However, there is some information that can be utilized.

The plan quality optimization engine 208 or the objective function updating component 214 can estimate an approximation of the Jacobian based on intuitive relations between the one or more parameters of the objective function and the one or more quality metrics. There is some intuition on how modifying parameters of the optimization objective j affects some of the metric values $q_i$. The plan quality optimization engine 208 or the objective function updating component 214 can use this intuition information to determine an approximation $$\overline{a}_{*j}^{int}$$

for $\overline{a}_{+j}$. The more information can be extracted from the optimization setup, the better this approximation will be. In some implementations, a separate algorithm, e.g., an artificial-intelligence-based algorithm or a learning model, can approximate the intuitive changes in the quality metrics $q_i$ (due to a change in the parameter(s) or weight of the $j^{th}$ optimization objective), and provide the approximated changes in the quality metrics $q_i$ to the plan quality optimization engine 208 or the objective function updating component 214. The plan quality optimization engine 208 or the objective function updating component 214 can use the input to determine approximation $$\overline{a}_{*j}^{int}$$

for each $\overline{a}_{+j}$.

One source of the intuition is the objective placement used for the optimization problem. Many of the metric values are evaluated in the same DVH space as the optimization objectives. It also makes sense to set up the optimization objectives so that they closely correspond to the clinical objectives. For example, in the clinical objectives set of Table 1, the clinical objective P2.2 specifies that for the PTV, D99.0%>46.5 Gy. The achieved value of this clinical objective can be used as one of the metrics in in the quality metric $\bar{q}$. Let $q_4$ be the quality metric corresponding to the achieved value of this objective. One way to drive this clinical objective (or the corresponding quality metric $q_4$) is to defined or construct an optimization objective term, e.g., $c_4$, in the objective function with dose and volume positions ($d_j$=46.5 Gy, $v_j$=99.0%) that closely correspond to the values specified in the clinical objective. This objective would now be one of the N optimization objectives, say j=4. Now by intuition, one would expect that by increasing the weight of optimization objective for j=4, one would increase the metric $q_{i=4}$. This way by intuition one can deduce information for or the value of $a_{4,4}$. Similarly, one can expect that increasing the dose for PTV through the optimization objective with index j=4 will increase the dose for organs also. By intuition one can then add some penalties for elements corresponding to organs in the vector $\bar{a}_{+4}$. In addition, if optimization engine can provide accurate cost information $c_j$ for the optimization objectives, the plan quality optimization engine 208 or the objective function updating component 214 can utilize this information to deduce how much the optimization objective will negatively affect other quality metrics in the quality metric vector $\bar{q}$. Also, information of structure overlaps can be utilized. No matter what the source of the intuition information, combining this information gives the approximation $$\bar{a}_{*j}^{int}.$$

However, the intuition $$\bar{a}_{*j}^{int}$$

is likely not to be an accurate approximation due to the complicated nature of $\delta\bar{q}/\delta\bar{w}$ and the coarse nature of the approximation.

To remedy the errors or inaccuracies of $$\bar{a}_{*j}^{int},$$

the plan quality optimization engine 208 or the objective function updating component 214 can determine and use another approximation for $\bar{a}_{+j}$. This second approximation can be based on information gathered between two consecutive calls of the plan quality optimization engine 208 or the objective function updating component 214 (or consecutive adjustments/modifications of the objective function parameters). In other words, the plan quality optimization engine 208 or the objective function updating component 214 can estimate a second approximation of the Jacobian based on one or more previous variations of the one or more quality metrics due to previous adjustments of the one or more parameters of the objective function. This second approximation of the vector $\bar{a}_{+j}$ can be referred to as an optimization-history based approximation and can be denoted as $$\bar{a}_{*j}^{hist}.$$

The plan quality optimization engine 208 or the objective function updating component 214 can determine this approximation by collecting information of how the changes introduced to $\bar{w}$ (or more generally to parameters of the objective function) are actually affecting $\bar{q}$ during the optimization of the radiation treatment plan. Whenever the plan quality optimization engine 208 or the objective function updating component 214 manipulates or modifies an optimization objective j (or parameters thereof), the plan quality optimization engine 208 or the objective function updating component 214 can calculate how $\bar{q}$ changed after the modification. The historical measurement of $\bar{a}_{+j}$ satisfies $$\bar{a}_{*j}^{meas}$$

$\propto\bar{q}^{new}-\bar{q}^{prev}$. Here $\bar{q}^{prev}$ is the quality metric vector before the modification and $\bar{q}^{new}$ is the quality metric vector after the modification and the objective function optimization by the objective function optimization engine 204. Given new and previous measurements, the plan quality optimization engine 208 or the objective function updating component 214 can implement or use a prediction approach, e.g., using a Kalman filter or other prediction methods, to predict new $$\bar{a}_{*j}^{hist}$$

based on historical information of $$\bar{a}_{*j}^{hist}.$$

In some implementations, the plan quality optimization engine 208 or the objective function updating component 214 can collect quality metric values $\bar{q}^t$ from all previous iterations t. Given that $\bar{q}^t$ inherently depends on the weight vector $\bar{w}^t$ (and/or other parameters of the objective function) at iteration t, the plan quality optimization engine 208 or the objective function updating component 214 can construct a regression model from the history data. The regression model can be a linear model of the form $$q_i = w_1 b_{i1} + w_2 b_{i2} + \ldots + w_N b_{iN},$$

for each $q_i$. The regression model can be a linear model where w; is replaced by a function $f(w_j)$. The plan quality optimization engine 208 or the objective function updating component 214 can use the regression model to predict $$\bar{a}_{*j}^{hist}.$$

Having both the intuition approximation $$\bar{a}_{*j}^{int}$$

and the optimization-history based approximation $$\bar{a}_{*j}^{hist},$$

the plan quality optimization engine 208 or the objective function updating component 214 can combine both approximations to form a final prediction $$\bar{a}_{*j} = \bar{a}_{*j}^{final} = \alpha_j \bar{a}_{*j}^{hist} + (1 - \alpha_j)\bar{a}_{*j}^{int}.$$

Here coefficient α represents a confidence in the optimization-history based approximation of the optimization objective with index j. The plan quality optimization engine 208 or the objective function updating component 214 can adjust this confidence based on how much history information has been collected. The more times the optimization objectives have been manipulated or modified, the more we trust can be put into optimization history based prediction (e.g., larger $\alpha_j$). Conversely, when not much historical information has been collected, the value of $\alpha_j$ can be relatively low, and the prediction will be mostly based on intuition. This approach means that as the overall optimization of the radiation treatment plan progresses, the plan quality optimization engine 208 or the objective function updating component 214 can make more accurate predictions. Following the same approach for various vectors $\bar{\alpha}_{+j}$, the plan quality optimization engine 208 or the objective function updating component 214 can determine a third (or final) approximation of the Jacobian as a weighted sum of the intuition approximation and the optimization-history-based approximation, and adjust the one or more parameters of the objective function based on the third approximation of the Jacobian.

It is to be pointed out that collecting the information for $$\bar{a}_{*j}^{hist}$$

relies on adjusting or modifying a single optimization objective at a time. Hence, even though all $\bar{a}_{+j}$ together constitute an approximation for the whole Jacobian $\delta\bar{q}/\delta\bar{w}$ determining the direct gradient of S with respect to $\bar{w}$ (and/or other parameters of the objective function) by chain-rule $$\frac{\delta S}{\delta \bar{w}} = \frac{\delta S}{\delta \bar{q}} \frac{\delta \bar{q}}{\delta \bar{w}}$$

may not be used. If the chain-rule is used, then collecting and using data for $$\bar{a}_{*j}^{hist}$$

may not be employed. In other words, the chain-rule involves modifying parameters of multiple optimization objectives at the same time, which makes it difficult to collect the information for $$\bar{a}_{*j}^{hist}$$

which relates to adjusting or modifying a single optimization objective at a time. The plan quality optimization engine 208 or the objective function updating component 214 can adjust or modify the parameter(s) of a single optimization objective at a time. In other words, the plan quality optimization engine 208 or the objective function updating component 214 can use the predicted or constructed $\bar{a}_{+j}$ to make decision on how to adjust $\bar{w}$ (and/or other parameters of the objective function).

Having a predicted vector $\bar{a}_{+j} \in R^M$ and the current values of the metric $\bar{q} \in R^M$, the plan quality optimization engine 208 or the objective function updating component 214 can determine or construct a prediction for new metric values if the parameter(s) of the optimization objective with index j were to be adjusted. The plan quality optimization engine 208 or the objective function updating component 214 can determine or calculate the prediction $\bar{q}^{p,j}$ as $$\bar{q}^{p,j} = \bar{q} + \delta_j \bar{a}_{*j}.$$

The coefficient $\delta_j$ indicates how much the weight w (and/or other parameter associated with the $j^{th}$ optimization objective) should be adjusted or modified. If $\delta_j$ is positive, the weight $w_j$ is to be increased. If $\delta_j$ is negative, the weight $w_j$ (and/or other parameter associated with the $j^{th}$ optimization objective) is to be decreased. The plan quality optimization engine 208 or the objective function updating component 214 can choose the scaler $\delta_j$ so that $S(\bar{q}^{p,j})$ is maximized or increased. The plan quality optimization engine 208 or the objective function updating component 214 can use a line search algorithm to determine the scaler $\delta_j$. The plan quality optimization engine 208 or the objective function updating component 214 can determine a prediction $$S_j^p = S(\bar{q}^{p,j}, j)$$

for all optimization objectives with index j∈[1, N] with optimal or best $\delta_j$ (e.g., based on line search algorithm). The plan quality optimization engine 208 or the objective function updating component 214 can determine the best optimization objective for which to adjust the constant parameter(s) (e.g., corresponding weight) by comparing the quality scores achieved by adjusting the parameters of different optimization objectives and selecting the optimization objective associated with the best predicted quality score S. The plan quality optimization engine 208 or the objective function updating component 214 can adjust or modify the parameter(s) of the optimization objective using the value of $\delta_j$ that produced the best or highest score S.

In some implementations, the plan quality optimization engine 208 or the objective function updating component 214 can perform parameter adjustment or modification for multiple optimization objectives at the same time. However, as discussed above, collecting history information may not be viable. Accordingly, the plan quality optimization engine 208 or the objective function updating component 214 can initially use $$\overline{a}^{int}_{*j}$$

to calculate the direct gradient $$\frac{\delta S}{\delta \overline{w}} = \frac{\delta S}{\delta \overline{q}} \frac{\delta \overline{q}}{\delta \overline{w}}$$

for the first few iterations, and then switch to using the predictions $\overline{q}^{p,j}$ as discussed above. The intuition approximation may be good enough at the start of the optimization, however it is useful to change to the single objective manipulation after few iterations.

The embodiments described herein provide performance, flexibility and allow for tunability. The embodiment provide better performance as they allow to modify larger amounts of optimization objectives in fewer iterations in order to optimize $S(\overline{q})$ more quickly. The embodiments provide flexibility as they support any form of $S(\overline{q})$ and are not limited to a certain plan quality score function.

The embodiment also offer better tunability of the decision logic associated with the plan quality optimization engine 208 or the objective function updating component 214. The tuning is reduced to deriving the metric trade-off information that is stored in $a_{ij}$. For example, for neural network approaches that aim for similar adjustments of the objective function parameters, tuning requires long self-training simulations with large amount of work in increasing training data sets.

Compared to optimization methods that use direct gradient calculations from $S(\overline{q})$ to fluence for optimizing the plan, the proposed methods allow the definition of $S(\overline{q})$ to be incomplete and still produce good quality plans. In the proposed method the $S(\overline{q})$ related objectives can be directly mixed with some standard objectives, such as normal-tissue-objectives, fluence smoothing objectives, MU objectives or leaf-movement objectives C. Generating Plan Quality Score Functions for Radiation Treatment Planning Another technical challenge associated with improving the quality of radiotherapy treatment plans using a plan quality score function is how to generate a total plan quality scoring metric to be used in automatic radiotherapy treatment planning optimization and evaluation. In other words, given a prioritized list of clinical objectives as input, which can be a partially incomplete description of the clinical desire and for which the scoring metric hasn't been defined, how to define or generate a continuous quality metric variable and generate a quality score function defined over the continuous quality metric variable.

Radiotherapy treatment plans can be been optimized by either minimizing a total objective function defined using a set of optimization objectives, or by maximizing a total plan quality score of the treatment plan. The core input in designing or determining any radiation treatment plan (apart from the patient data) is usually a set of clinical objectives which can be supplemented with additional goals/objectives for the optimal plan, dose or fluence. Embodiments described below allow for automatically generating a continuous plan quality score function based on indications of the clinical objectives. The relative priorities or importance of various clinical objectives can be integrated or incorporated in the plan quality score function. As such, the plan quality score function can lead to determining a plan that achieves the various clinical objectives while prioritizing the achievement of the higher-priority objectives.

Figure 4:
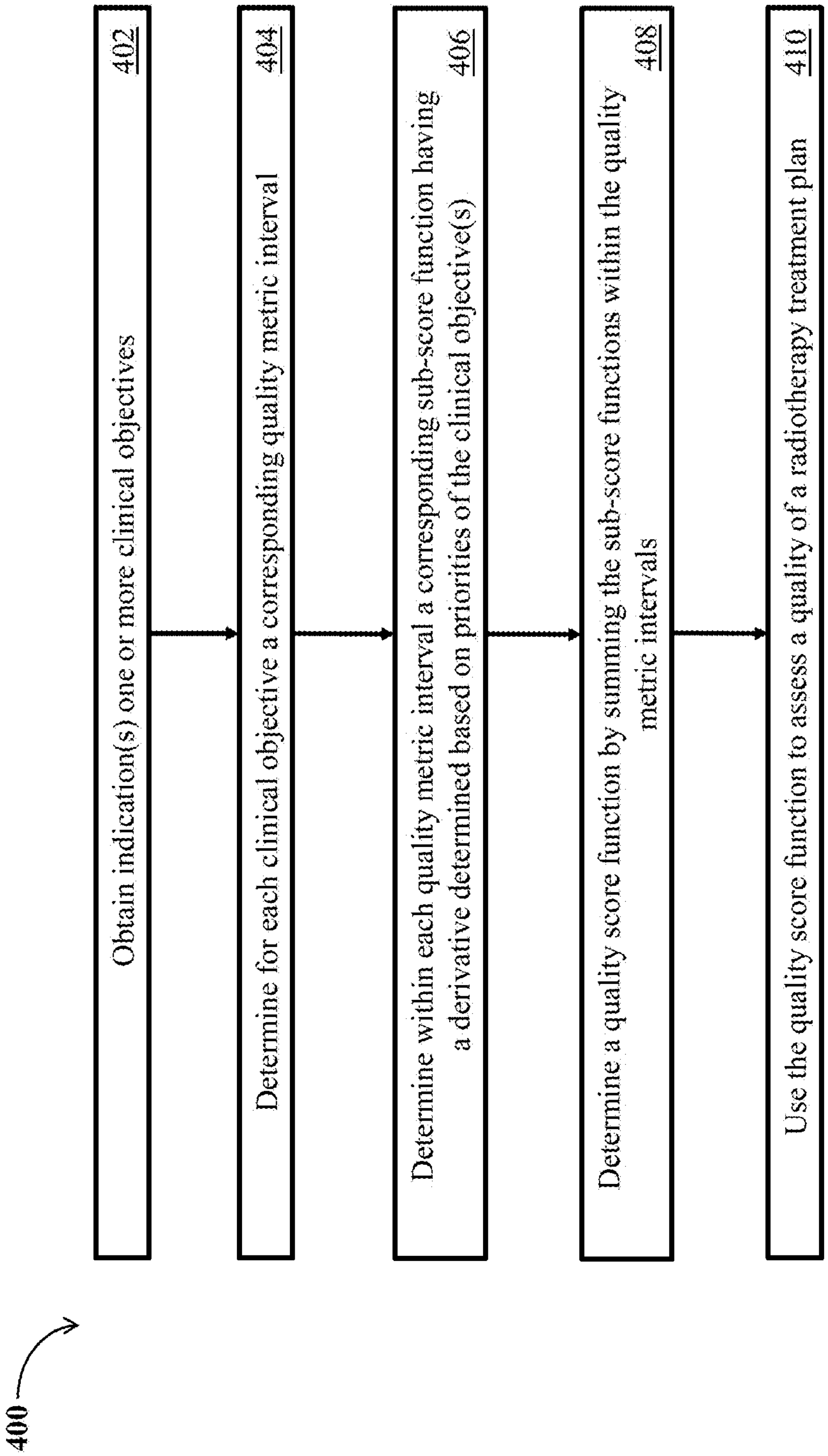
FIG. 4 is a flowchart illustrating a method of generating a plan quality score function, according to an embodiment.

Referring now to FIG. 4, a flow chart illustrating a method 400 for generating a plan quality score function is shown, according to an embodiment. The method 400 can be implemented or executed by the radiotherapy planning system 110, the one or more processors 154 and/or the score function generation component 206. In brief overview, the method 400 can include the score function generation component 206 obtaining one or more indications of one or more clinical objectives (STEP 402) and determining for each clinical objective a corresponding quality metric interval (STEP 404). The method 400 can include the score function generation component 206 determining within each quality metric interval a corresponding sub-score function having a derivative determined based on one or more priorities of the one or more clinical objectives (STEP 406), and determining or generating a quality score function by summing up the sub-score functions within the quality metric intervals (STEP 408). The method 400 can include the plan quality optimization engine 208 using the quality score function to assess a quality of a radiotherapy treatment plan (STEP 410).

The method 400 can include the score function generation component 206 obtaining or receiving one or more indications of one or more clinical objectives (STEP 402). The score function generation component 206 can receive the one or more indications of the one or more clinical objectives as input. Referring back to Table 1, example clinical objectives and indications thereof are listed in Table 1. Each clinical objective can include or can represent a constraint on a radiation dose distribution within a corresponding anatomical structure. For example, the first clinical objective in Table 1 specifies a constraint on the radiation distribution within the left parotid gland, the second clinical objective specifies a constraint on the radiation distribution within the right parotid gland, the next three clinical objectives specify constraints on the radiation distribution within the PTV, and the last clinical objective in Table 1 specifies a constraint on the radiation distribution within the spinal cord.

In some implementations, the one or more indications of the one or more clinical objectives can include, for each clinical objective, an indication of a priority of that clinical objective. For example, the priority of the first clinical objective "Lt Parotid" in Table 1 is indicated as P1.1, which means that the clinical objective is in priority group 1 and it is the first in that group (or has the highest priority in that priority group 1). The priority indication P1.2 for the second clinical objective "Rt Parotid" in Table 1 implies that the second objective has the second highest priority in priority group 1. The priority indications for the other four clinical objectives are listed as P2.1, P2.2, P2.3 and P2.4 indicating that these clinical objectives are in priority group 2 and with decreasing priorities in this group. For instance, P2.1, P2.2, P2.3 and P2.4 are indicative of the first priority, the second priority, the third priority and the fourth priority, respectively, in priority group 2. Priority group 1 is assumed to have higher priorities here than priority group 2. In some implementations, the priorities of the clinical objectives can be indicated or defined differently (e.g., different priorities with no priority groups defined).

For each clinical objective (or some clinical objectives) the indication of the clinical objective can include an inequality related to a radiation dose distribution within a corresponding anatomical structure where the inequality can be defined in terms of a desired radiation dose value. For example, the clinical objective "Lt Parotid" states that D50.0%≤20.00 Gy, which means that the radiation dose for 50% value of the volume of the left parotid gland should be less than or equal 20 Gy. This defines the quality metric axis 'q' for this clinical objective to be D50% and defines the goal value in that axis to be equal to 20.00 Gy. A similar quality metric axis 'q' and similar goal value are defined for the "Rt Parotid" clinical objective. Similarly, the clinical "Cord" for the spinal cord states that Dmax (0.0%)<40.00 Gy, which defines a quality axis 'q' to be the maximum dose value in that structure with goal or target value equal to 40.00 Gy. Three clinical objectives, with priorities P2.1, P2.2 and P2.3, are provided or set for the PTV. The first among these clinical objectives states that D90%≥50.00 Gy, which defines the quality metric axis 'q' for this clinical objective to be D90% and the goal value in that axis to be equal to 50.00 Gy. The second PTV objective states that D99%≥46.50 Gy, which defines the quality metric axis 'q' for this clinical objective to be D99% and the goal value in that axis to be equal to 46.50 Gy. The third PTV objective states that D20%≤55.00 Gy, which defines the quality metric axis 'q' for this clinical objective to be D20% and the goal value in that axis to be equal to 55.00 Gy.

The method 400 can include the score function generation component 206 determining, for each clinical objective, a corresponding quality metric interval (STEP 404). For each clinical objective, the score function generation component 206 can determine the corresponding quality metric interval using the goal value in 'q' axis for that clinical objective. For example, for the "Lt Parotid" and "Rt Parotid" objectives, the score function generation component 206 can determine the corresponding quality metric intervals using the goal value 20.00 Gy. For the first PTV objectives, the score function generation component 206 can determine the corresponding quality metric intervals using the goal values 50.00 Gy, 46.50 Gy and 55.00 Gy, respectively. For the "Cord" objective, the score function generation component 206 can determine the corresponding quality metric interval using the goal values 40.00 Gy. In other words, for each clinical objective, the corresponding goal value can be used to determine the start or end (depending on whether the inequality include > or ≥, or the inequality includes < or ≤) of the corresponding quality metric interval. For instance, if the inequality has > or ≥, the goal value is used to determine the end of the corresponding quality metric interval, and if the inequality has < or ≤, the goal value is used to determine the start of the corresponding quality metric interval.

In some implementations, the clinical objectives can include an additional "acceptable variation" value that is defined. This can be defined in the same quality axis q, as the goal value. It basically indicates that clinically there is a point in 'q' that is less desirable than the goal value but still viable enough to make the treatment plan acceptable for treatment. In some implementations, an additional "expected" value can be defined or provided as input. This is not part of a clinical decision-making protocols but more like a more desirable value, "beyond" the goal value which would make the radiation treatment plan more acceptable if achieved.

In some implementations, the score function generation component 206 can define a set of points in quality metric axis for each clinical objectives, such as q[must], q[goal], q[expected], q[reach], q[post_reach]. The points can be in monotonic order of how "demanding" it is to achieve the value, or how clinically desirable the value is. In some implementations, at most 3 of those q-value points are defined (e.g., based on input). In some implementations, more q-value points can be given or defined if they hold clinically relevant information that helps the optimal plan to be more desirable. One example could be a point that defines q values that describe robust planning in an adaptive workflow. As an example, the score function generation component 206 can define the following intervals within the q axis (or can divide the q axis into the following intervals) defined by the above listed q-points:

interval 1: {q[ad inf], q[must]}
interval 2: {q[must], q[goal]}
interval 3: {q[goal], q[expected]}
interval 4: {q[expected], q[reach]}
interval 5: {q[reach], q[post_reach]}

Other intervals can be added if additional q-points are defined. By default, the q[goal] is expected to be always defined. Additionally, the clinical goal input might have an acceptable variation value defined per goal. In this case, the score function generation component 206 can use the q[must] value to represent acceptable variation value. Otherwise, it can use q[must]=q[goal]. Additionally, the expected values q[expected] are sometimes available depending on the workflow. It could be any value that the user normally expects to be met in certain cases. It can also come from algorithmic calculations or templates. Otherwise, the score function generation component 206 can automatically calculate a q[expected] value that is slightly more demanding than the q[goal] value. The q[reach] and q[post_reach] values are typically never given in clinical goal input, so the score function generation component 206 automatically can calculate them. One approximation is to use half of the q[goal] value for organs-at-risk structures and q[goal] value for targets to represent q[reach] and q[post_reach]. In some implementations, the score function generation component 206 can determine or defined the reach values so that the structure overlaps in patient geometry are considered. The q[ad inf] can be an arbitrary cut-off point for defining a reasonable range for score calculation. It can be 0 (or start of the range) or "a large number" (for end of the range) depending on the type of the goal.

Figure 5:
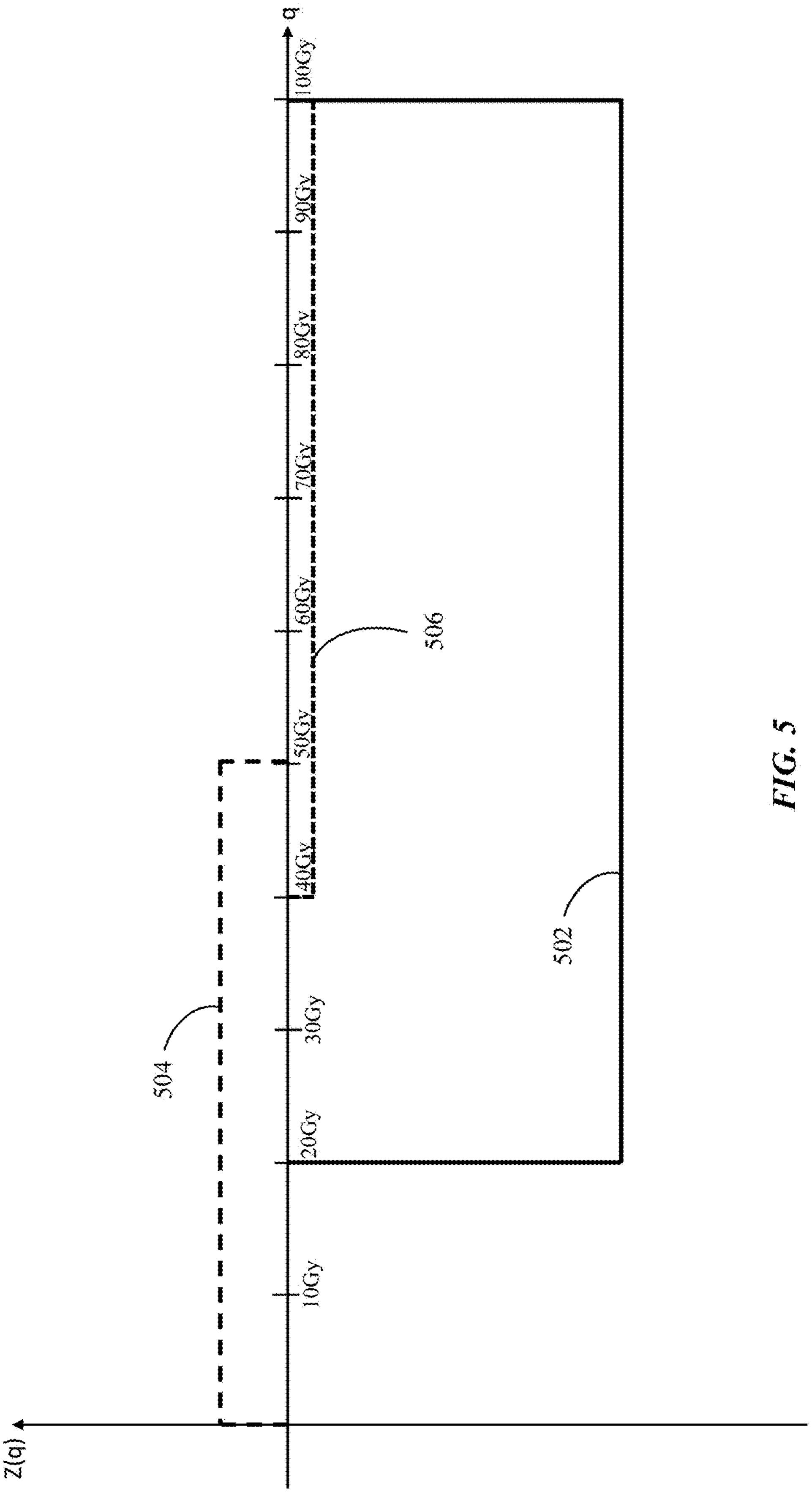
FIG. 5 show example score density functions for various clinical objectives, according to an embodiment.

In some implementations, the score function generation component 206 can determine a single interval within the q range, for example, using the q[goal] and q[ad inf] for each clinical objective, as depicted in FIGS. 4 and 5. For example, and referring to FIGS. 5 and 6, a total q range [0, 100.00 Gy] is assumed. For the "Lt Parotid" objective, the q interval [20.00 Gy, 100.00 Gy] is determined. For the first PTV objective, the q interval [0, 50.00 Gy] is determined, and for the "Cord" objective, the q interval [40.00 Gy, 100.00 Gy] is determined. Note that the value 0 is as q[ad inf] for the first PTV objective, and the value 100.00 Gy is used as as q[ad inf] for the "Lt Parotid" and "cord" objectives.

The method 400 can include the score function generation component 206 determining, for each clinical objective, a corresponding sub-score function within a quality metric interval associated with the clinical objective, where the corresponding sub-score function has a derivative determined based on priorities of the clinical objectives (STEP 406). Let q be a quality metric vector corresponding to M clinical goals, where $q=(q_1, q_2, \ldots, q_M)$. Each $q_i$ value can represent a metric value achieved by the radiation treatment plan P. The plan quality score function S(q) is desired to define a quality score for any quality metric vector q. In other words, distinct radiation treatment plans can produce different quality metric vectors q, and the plan quality score function S(q) should be defined or formulated in a way that it can be calculated for the various quality metric vectors.

The plan quality score function S(q) can be viewed or defined as $S(q)=S_1(q_1)+S_2(q_2)+ \ldots S_M(q_M)$. The plan quality score function S(q) is expected to represent a score metric as a function of achieved quality values in order to optimize or improve the quality of radiation treatment plans produced by the objective function optimization engine 204. The terms $S_1(q_1)$, $S_2(q_2)$ . . . $S_M(q_M)$ can be viewed as sub-scores (or sub-score functions) specific to different clinical objectives or goals. In other words, the sub-scores $S_1(q_1)$, $S_2(q_2)$ . . . $S_M(q_M)$ can represent the contributions of the various clinical objectives, respectively, to the plan quality score function S(q). In some implementations, the sub-score functions $S_1(q_1)$, $S_2(q_2)$ . . . $S_M(q_M)$ can be defined differently. For example, a sub-score function $S_i(q_i)$ can correspond to more than one clinical objective, or multiple sub-score functions can correspond to a single clinical objective (e.g., a sub-score function can partially reflect or represent the contribution of a single clinical objective to the plan quality score function.

The score function generation component 206 can determine, for each clinical goal, a corresponding sub-score function within a quality metric interval associated with the clinical objective such that the sub-score function represents the corresponding term $S_i(q_i)$ (where $S(q)=S_1(q_1)+S_2(q_2)+$ . . . $S_M(q_M)$) within the quality metric interval associated with the clinical objective. For example, the score function generation component 206 can determine, for each clinical goal, a corresponding sub-score function within the quality metric interval [$q_i$[ad inf], $q_i$[goal]] or [$q_i$[goal], $q_i$[ad inf]]. Note that the score function generation component 206 can determine, for each clinical objective, the intervals discussed above. In some implementations, the score function generation component 206 can determine, for each clinical goal, a corresponding monotonic function (as the sub-score function) within the quality metric interval associated with the clinical objective. In some implementations, the score function generation component 206 can determine, for each clinical goal, a corresponding linear function (as the sub-score function) within the quality metric interval associated with the clinical objective.

The score function generation component 206 can determine the derivative(s), or properties the derivative(s), of the sub-score function for a clinical objective based on the type of inequality describing the clinical objective and/or the priority (or priority indication) of the clinical objective. Determining the derivative(s) of the sub-score function can include determining the minimum derivative, the maximum derivative, the average derivative or all derivatives of the sub-score function within the quality metric interval associated with the clinical objective. If the inequality has > or ≥, the score function generation component 206 can determine the derivative(s) of the sub-score function to be positive, and if the inequality has < or ≤, the score function generation component 206 can determine the derivative(s) of the sub-score function to be negative. Also, the score function generation component 206 can assign a relatively high magnitude to the derivative(s) for clinical objectives with relatively high priority, and can assign a relatively low magnitude to the derivative(s) for clinical objectives with relatively low priority. The higher is the priority of the clinical objective, the higher is the magnitude of the derivative(s) of the corresponding sub-score function. As such, lower priority objectives will not be achieved by deviating away from higher-priority clinical objectives.

Let a first and second clinical goals have first and second priorities (or be associated with first and second priority groups), respectively, where the first priority is higher than the second priority or the first priority group is of higher priorities than the second priority group. In some implementations, the score function generation component 206 can determine a first and second sub-score functions for the first and second clinical goals, such that the minimum derivative magnitude of the first sub-score function (within a first corresponding quality metric interval) is larger than the maximum (or the average) derivative magnitude of the second sub-score function (within a second corresponding quality metric interval). In some implementations, the score function generation component 206 can determine the first and second sub-score functions, such that the average derivative magnitude of the first sub-score function (within the first corresponding quality metric interval) is larger than the maximum (or average) derivative magnitude of the second sub-score function (within the second corresponding quality metric interval). In some implementations, the score function generation component 206 can determine the first and second sub-score functions, such that the derivative magnitudes of the first sub-score function (within the first corresponding quality metric interval) fall within a first range and the derivative magnitudes of the second sub-score function (within the second corresponding quality metric interval) fall within a second range different from the first range. In the case where the sub-score functions are linear functions within the corresponding quality metric intervals, the score function generation component 206 can determine the slope for each sub-score function based on properties of the clinical objectives, such as the type of corresponding constraints (or inequalities) and/or the corresponding priorities.

In some implementations, the score function generation component 206 can define or determine, for each clinical objective, a corresponding score density function $Z_i(q_i)$ within the quality metric interval associated with the clinical objective, e.g., [q[ad inf], q[goal]] or [q[goal], q[ad inf]]. In some implementations, the score function generation component 206 can define or determine, for each sub-score function $S_i(q_i)$, the corresponding score density function $Z_i(q_i)$ within the quality metric interval associated with the clinical objective related to the sub-score function $S_i(q_i)$. The score density function $Z_i(q_i)$ can be indicative of, or can represent, the derivative function for the corresponding sub-score function $S_i(q_i)$. In the case where the sub-score functions are linear functions within the corresponding quality metric intervals, the score density function $Z_i(q_i)$ can be a constant function within the quality metric interval associated with the corresponding clinical objective, and its value can be indicative of or representing the slope of the corresponding linear function. The score function generation component 206 can determine the sub-score function $S_i(q_i)$ with the quality metric interval associated with the corresponding clinical objective by integrating the score density function $Z_i(q_i)$, such that the integrated score at achieved value q[ach] would be $S_i(q_i$[ach])=Integral of $Z_i(q_i)$ over $q_i$=[0, q[ach]]. The value of $Z_i(q_i)$ can be negative or positive depending on the type of inequality associated with the clinical objective (e.g., < or >).

Referring now to FIG. 5, example score density functions for the first, third and last clinical objectives in Table 1 are shown, according to an embodiment. The plots 502, 504 and 506 represent the score density functions for the first, third and last clinical objectives in Table 1, respectively. Assuming linear sub-score density functions, the plots 502, 504 and 506 represent constant score density functions within corresponding quality metric intervals. The score density functions can be equal to zero outside the corresponding q-intervals. Each score density function can be viewed as representing or indicative of the priority of the corresponding clinical objective, the corresponding q-interval and/or the type of inequality (or type of clinical objective). In other words the score density function $Z_i(q_i)=Z_i(q_i$, q-interval, priority, location or rank within priority group, type of constraint). In some implementations, the score function generation component 206 can normalize the values of $Z_i(q_i)$ in the q-intervals, so that certain aspects of the plan quality and prioritized list are considered. Accordingly, the resulting plan quality score function S(q) will automatically drive the optimization towards the clinical objectives. The plan quality score function S(q) can be viewed as ranking the clinical objectives based on the contribution of each objective to the plan quality score function.

Generally, the higher the importance or priority of the clinical objective, the more score its' metric gives when achieving it. Also, the higher is the importance or priority of the clinical objective, the more the plan quality score function S(q) will decrease when deviating away from the clinical objective.

Figure 6:
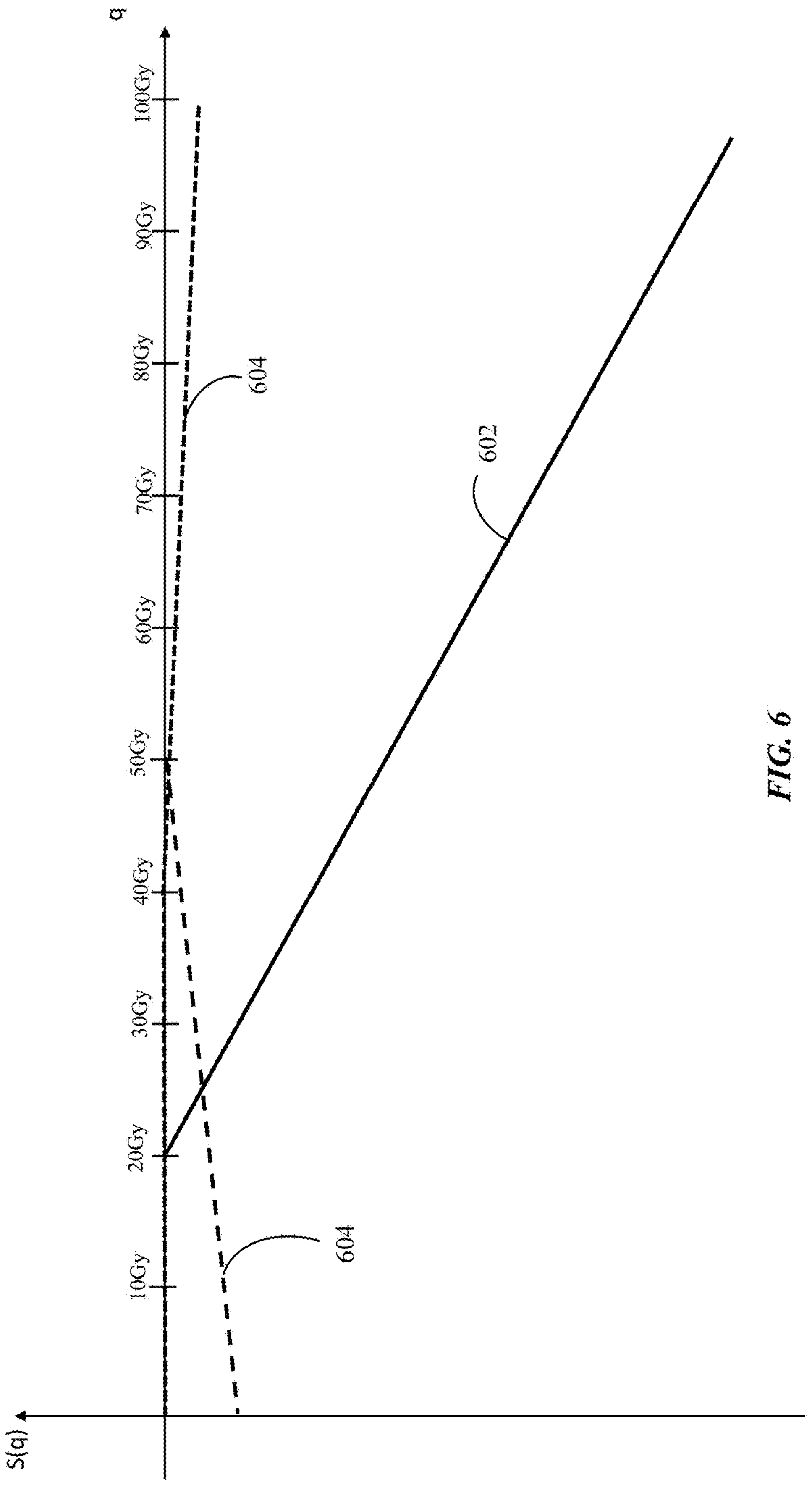
FIG. 6 show example sub-score functions for various clinical objectives, according to an embodiment.

Referring now to FIG. 6, example sub-score linear functions for the first, third and last clinical objectives in Table 1 are shown, according to an embodiment. The plots 602, 604 and 606 represent the sub-score linear functions for the first, third and last clinical objectives in Table 1, respectively. The sub-score linear functions can be determined by integrating the score density functions 501, 504 and 506, respectively, or by directly determining the slope (e.g., based on the priorities and the types of the clinical objectives) for each sub-score linear function. Each sub-score linear function can be viewed as representing or indicative of the contribution of the corresponding clinical objective to the plan quality score function S(q) within the corresponding q-interval. Each of the sub-score linear functions can be assumed to be constant (e.g., equal to 0) outside the corresponding q-interval determined at step 404 (e.g., outside the q-interval [q[ad inf], q[goal]] or [q[goal], q[ad inf]])

In some implementations, the score function generation component 206 can normalize the score density functions $Z_i(q_i)$ or the slopes of the sub-score linear function so that the increase or decrease in the score S(q) when moving towards (or moving away from) achieving the goal values q[must] or a[goal] of all 4 priority 2 clinical objectives (P2.1, P2.2, P2.3, P2.4) will not exceed the increase or decrease in the score S(q) when moving towards (or moving away from) achieving the goal values q[must] or q[goal] of the 2 priority 1 clinical objectives (P1.1, P1.2). As depicted in FIG. 5, the constant value of the score density function 502 is greater than the sum of the values of the score density functions 5004 and 506. Also, the magnitude of the slope of sub-score function 606 is greater than the sum of magnitudes of the slopes of the sub-score functions 604 and 606. As such, the radiotherapy treatment plan optimization will not ruin or jeopardize the clinical objectives in priority group 1 while trying to achieve the desired values of clinical objectives in the in priority group 2. Since this is automatically generated by the score function generation component 206, this property will hold even when the user adds/removes clinical objectives to/from the clinical objective list.

The method can include the score function generation component 206 determining or generating a quality score function by summing up the linear functions within the quality metric intervals (STEP 408). For example, referring again to FIG. 6, the score function generation component 206 can aggregate the sub-score functions 602, 604 and 606 as well as other sub-score functions (not shown in FIG. 6) corresponding to the rest of the clinical objectives in Table 1 to determine the final plan quality score function S(q). The resulting plan quality score function S(q) can be a piecewise linear function.

While FIGS. 5 and 6 depict an example of constant score density functions and linear sub-score functions, the sub-score density functions can be non-linear monotonic functions and the corresponding score density functions can be non-constant functions within the corresponding quality metric intervals. In some implementations, nonlinear monotonic functions (e.g., instead of linear functions) can be used to represent different sub-score functions for different clinical objectives within corresponding q-intervals. For example, logarithmic functions and/or exponential functions can be used as sub-score functions instead of the linear functions. In such case, the priorities can be preserved by enforcing relationships between the minimum derivative magnitude, the maximum derivative magnitude and/or the average derivative magnitude for different sub-score functions associated with different priorities. For example, the higher is the priority of the clinical objective, the higher is the magnitude of the minimum derivative magnitude, maximum derivative magnitude and/or average derivative magnitude of the corresponding sub-score function within the corresponding q-interval. The final plan quality score function S(q) can be determined in the same way, e.g., by summing up the sub-score functions for various clinical objectives.

In some implementations where supplementary clinical objectives are added to the input list, the score function generation component 206 can properly scale or determine the slopes (or derivatives) of the sub-score functions for the supplementary clinical objectives without breaking the general properties of the scoring metric or the plan quality score function. This makes the described approach very flexible to be used in optimization.

The method 400 can include the plan quality optimization engine 208 using the quality score function to assess a quality of a radiotherapy treatment plan (STEP 410). As described above with regard to FIG. 3, the plan quality optimization engine 208 can evaluate the plan quality score function S(q) for each radiotherapy treatment plan produced by the objective function optimization engine 204. The plan quality optimization engine 208 can determine an adjustment of the parameters of the objective function based on the plan quality score function S(q) as discussed above in Section B. The plan quality optimization engine 208 can assess a first quality of a first radiotherapy plan produced by optimizing the objective function by computing a value of the quality score function based on one or more parameters of the first radiotherapy treatment plan, and adjust the one or more parameters of the objective function in a way to increase a second quality score of a second radiotherapy treatment plan produced by optimizing the objective function with the adjusted one or more parameters.

According to embodiments described herein, a score metric for assessing the quality of radiotherapy treatment plans is automatically generated based on input indicative of clinical objectives. The score metric is automatically ranked between all various clinical objectives so that it can be used to optimize the best possible plan as such. The score metrics are determined over the whole quality metric range. The score metric can be automatically re-normalized or re-scaled when supplementary clinical objectives are added. As such, the added clinical objectives won't change the original behavior if not allowed. The score metric automatically takes patient geometry into account when calculating desired quality values. Finally, given that the quality score metric is automatically determined, the user or the planner does not have to provide separate score values for various objectives and various quality metric points. This reduces the amount of input data needed and reduces the burden on the user.

Each method described in this disclosure can be carried out by computer code instructions stored on computer-readable medium. The computer code instructions, when executed by one or more processors of a computing device, can cause the computing device to perform that method.

While the disclosure has been particularly shown and described with reference to specific embodiments, it should be understood by those skilled in the art that various changes in form and detail may be made therein without departing from the spirit and scope of the invention described in this disclosure.

While this disclosure contains many specific embodiment details, these should not be construed as limitations on the scope of any inventions or of what may be claimed, but rather as descriptions of features specific to particular embodiments of particular inventions. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

What is claimed is:

1. A method of radiation treatment planning comprising:

receiving, by one or more processors, one or more indications of one or more clinical objectives for a radiotherapy treatment plan;

determining, by the one or more processors, for each clinical objective, a corresponding quality metric interval;

determining, by the one or more processors, within each quality metric interval, a corresponding sub-score function having a derivative determined based on one or more priorities of the one or more clinical objectives;

determining, by the one or more processors, a quality score function for the radiotherapy treatment plan by aggregating sub-score functions within quality metric intervals corresponding to the one or more clinical objectives;

using, by the one or more processors, the quality score function to adjust one or more parameters of an objective function for optimizing the radiotherapy treatment plan; and transmitting, by the one or more processors, the optimized radiotherapy treatment plan to a radiation treatment device, whereby the one or more processors control at least one operational parameter of the radiation treatment device based on the optimized radiotherapy treatment plan.

2. The method of claim 1, wherein using the quality score function to adjust the one or more parameters of the objective function includes:

assessing a first quality of a first radiotherapy treatment plan produced by optimizing the objective function by computing a value of the quality score function based on one or more parameters of the first radiotherapy treatment plan; and adjusting the one or more parameters of the objective function in a way to increase a second quality score of a second radiotherapy treatment plan produced by optimizing the objective function with the adjusted one or more parameters.

3. The method of claim 1, wherein each clinical objective of the one or more clinical objectives includes a constraint on a radiation dose distribution within a corresponding anatomical structure.

4. The method of claim 1, wherein the one or more indications of the one or more clinical objectives include, for each clinical objective, an indication of a priority of the clinical objective.

5. The method of claim 4, further comprising:

determining, by the one or more processors, for each clinical objective, a derivative of the sub-score function within the quality metric interval corresponding to the clinical objective based on the indication of the priority of the clinical objective, the higher is the priority of the clinical objective the higher is a magnitude of the derivative of the sub-score function within the quality metric interval corresponding to the clinical objective.

6. The method of claim 1, wherein for each clinical objective of the one or more clinical objectives, the indication of the clinical objective includes an inequality related to a radiation dose distribution within a corresponding anatomical structure, the inequality defined in terms of a desired radiation dose value.

7. The method of claim 6, comprising:

determining, by the one or more processors, for each clinical objective, the corresponding quality metric interval using the desired radiation dose value.

8. The method of claim 6, comprising:

determining, by the one or more processors, for each clinical objective, a derivative of the sub-score function within the quality metric interval corresponding to the clinical objective based on a type of the inequality.

9. The method of claim 1, comprising:

determining, by the one or more processors, within each quality metric interval, a corresponding score density function; and determining, by the one or more processors, the sub-score function within each quality metric interval by integrating the corresponding score density function within the quality metric interval.

10. The method of claim 1, comprising:

determining, by the one or more processors, within each quality metric interval, the corresponding sub-score function as a linear function having a slope determined based the on one or more priorities of the one or more clinical objectives.

11. A radiation treatment planning system comprising:

one or more processors; and a memory to store computer code instructions, the computer code instructions when executed cause the one or more processors to:

receive one or more indications of one or more clinical objectives for a radiotherapy treatment plan;

determine for each clinical objective, a corresponding quality metric interval;

determine within each quality metric interval, a corresponding sub-score function having a derivative determined based on one or more priorities of the one or more clinical objectives;

determine a quality score function for the radiotherapy treatment plan by aggregating sub-score functions within quality metric intervals corresponding to the one or more clinical objectives;

use the quality score function to adjust one or more parameters of an objective function for optimizing the radiotherapy treatment plan; and transmit the optimized radiotherapy treatment plan to a radiation treatment device, whereby the one or more processors control at least one operational parameter of the radiation treatment device based on the optimized radiotherapy treatment plan.

12. The radiation treatment planning system of claim 11, wherein in using the quality score function to adjust the one or more parameters of the objective function, the one or more processors are further configured to:

assess a first quality of a first radiotherapy treatment plan produced by optimizing the objective function by computing a value of the quality score function based on one or more parameters of the first radiotherapy treatment plan; and adjust the one or more parameters of the objective function in a way to increase a second quality score of a second radiotherapy treatment plan produced by optimizing the objective function with the adjusted one or more parameters.

13. The radiation treatment planning system of claim 11, wherein each clinical objective of the one or more clinical objectives includes a constraint on a radiation dose distribution within a corresponding anatomical structure.

14. The radiation treatment planning system of claim 11, wherein the one or more indications of the one or more clinical objectives include, for each clinical objective, an indication of a priority of the clinical objective.

15. The radiation treatment planning system of claim 14, wherein the one or more processors are further configured to:

determine, for each clinical objective, a derivative of the sub-score function within the quality metric interval corresponding to the clinical objective based on the indication of the priority of the clinical objective, the higher is the priority of the clinical objective the higher is a magnitude of the derivative of the sub-score function within the quality metric interval corresponding to the clinical objective.

16. The radiation treatment planning system of claim 11, wherein for each clinical objective of the one or more clinical objectives, the indication of the clinical objective includes an inequality related to a radiation dose distribution within a corresponding anatomical structure, the inequality defined in terms of a desired radiation dose value.

17. The radiation treatment planning system of claim 16, wherein the one or more processors are configured to:

determine, for each clinical objective, the corresponding quality metric interval using the desired radiation dose value.

18. The radiation treatment planning system of claim 16, wherein the one or more processors are configured to:

determine, for each clinical objective, a derivative of the sub-score function within the quality metric interval corresponding to the clinical objective based on a type of the inequality.

19. The radiation treatment planning system of claim 11, wherein the one or more processors are configured to:

determine, within each quality metric interval, a corresponding score density function; and determine the sub-score function within each quality metric interval by integrating the corresponding score density function within the quality metric interval.

20. A non-transitory computer-readable medium including computer code instructions stored thereon, the computer code instructions when executed cause one or more processors to:

receive one or more indications of one or more clinical objectives for a radiotherapy treatment plan;

determine for each clinical objective, a corresponding quality metric interval;

determine within each quality metric interval, a corresponding sub-score function having a derivative determined based on one or more priorities of the one or more clinical objectives;

determine a quality score function for the radiotherapy treatment plan by aggregating sub-score functions within quality metric intervals corresponding to the one or more clinical objectives;

use the quality score function to adjust one or more parameters of an objective function for optimizing the radiotherapy treatment plan; and transmit the optimized radiotherapy treatment plan to a radiation treatment device, whereby the one or more processors control at least one operational parameter of the radiation treatment device based on the optimized radiotherapy treatment plan.

* * * * *